US007195757B2

(12) United States Patent
Curtiss, III et al.

(10) Patent No.: US 7,195,757 B2
(45) Date of Patent: Mar. 27, 2007

(54) MODULATION OF IMMUNE RESPONSES TO FOREIGN ANTIGENS EXPRESSED BY RECOMBINANT ATTENUATED BACTERIAL VECTORS

(75) Inventors: Roy Curtiss, III, St. Louis, MO (US); Ho Young Kang, Pusan (KR)

(73) Assignee: Washington University, St. Louis, MO (US)

( * ) Notice: Subject to any disclaimer, the term of this patent is extended or adjusted under 35 U.S.C. 154(b) by 361 days.

(21) Appl. No.: 10/414,533

(22) Filed: Apr. 15, 2003

(65) Prior Publication Data
US 2004/0120962 A1 Jun. 24, 2004

Related U.S. Application Data

(60) Provisional application No. 60/372,676, filed on Apr. 15, 2002, provisional application No. 60/373,669, filed on Apr. 18, 2002.

(51) Int. Cl.
*A01N 63/00* (2006.01)
(52) U.S. Cl. .................................................. 424/93.48
(58) Field of Classification Search .............. 424/93.48
See application file for complete search history.

(56) References Cited

U.S. PATENT DOCUMENTS 5,695,983 A * 12/1997 Miller et al. ............. 435/252.8

OTHER PUBLICATIONS

Chen et al (Infection and Immunity vol. 68, No. 6, pp. 3129-3139, Jun. 2000).*
U.S. Appl. No. 10/414,532, filed Apr. 15, 2003, Curtiss et al.
Bumler, Andreas J., et al., "Contribution of Fimbrial Operons to Attachment to and Invasion of Epithelial Cell Lines by *Salmonella typhimurium*," *Infection and Immunity*, Mayy 1996, p. 1862-1865, vol. 64, No. 5, American Society for Microbiology.
Bumler, Andreas J., et al., "Fimbrial Adhesins of *Salmonella typhimurium*," Mechanisms in the Pathogenesis of Enteric Diseases, Plnum Press, New York, 1997, pp. 149-158.
Bertani, G., "Studies on Lysogenesis: I. The Mode of Phage Liveration by Lysogenic *Escherichia coli*," vol. 62, 1951, p. 293-300.
Beveridge, Terry J., "Structures of Gram-Negative Cell Walls and Their Derived Membrane Vesicles," *Journal of Bacteriology*, vol. 181, No. 16, Aug. 1999, p. 4725-4733, American Society for Microbiology.
Bolivar, Francisco, et al., "Construction and Characterization of New Cloning Vehicles," *Gene*, 2(1977) 95-113, Elsevier/North Holland Biomedical Press, Amsterdam, Netherlands.
Botsford, James L., et al., "Cyclic AMP in Prokaryotes," *Microbiological Reviews*, vol. 56, No. 1, Mar. 1992, p. 100-122, American Society for Microbiology.

Breiman, Robert F., M.D., et al., "Emergence of Drug-Resistant Pneumococcal Infections in the United States," *The Journal of the American Medical Association*, vol. 27 (23) Jun. 1994, 1831-1835, American Medical Association.
Briles, David E., et al, "Immunization of Humans with Recombinant Pneumococcal Surface Protein A (rPspA) Elicits Antibodies That Passively Protect Mice from Fatal Infection with *Streptococcus pneumoniae* Bearing Heterologous PspA," *The Journal of Infectious Diseases* 2000; 182: 1694-701, Infectious Diseases Society of America.
Briles, David E., et al., "Pneumococcal Diversity: Considerations for New Vaccine Strategies with Emphasis on Pneumococcal Surface Protein A (PspA)," *Clinical Microbiology Reviews*, vol. 11, No. 4, Oct. 1998, p. 645-657, American Society for Microbiology.
Briles, David E., et al., "PspA, a protection-eliciting pneumococcal protein: immunogenicity of isolated native PspA in mice," *Vaccine*, vol. 14, No. 9, pp. 858-867, 1996, Elsevier Science Ltd., Great Britain.
Briles, David E., et al., "The potential for using protein vaccines to protect against otitis media caused by *Streptococcus pneumoniae*," *Vaccine*, 19 (2001) S87-S95, Elsevier Science Ltd.
Ciacci-Woolwine, Federica, et al., "Induction of Cytokine Synthesis by Flagella from Gram-Negative Bacteria May Be Dependent on the Activation or Differentiation State of Human Monocytes," *Infection and Immunity*, Oct. 1999, p. 5176-5185, vol. 67, No. 10, American Society for Microbiology.
Ciacci-Woolwine, Federica, et al., "*Salmonella* Flagellin Induces Tumor Necrosis Factor Alpha in a Human Promonocytic Cell Line," *Infection and Immunity*, Mar. 1998, p. 1127-1134, vol. 66, No. 3, American Society for Microbiology.
CIOFU, Oana, et al., "Chromosomal β-lactamase is packaged into membrane vesicles and secreted from *Pseudomonas aeruginosa*," *Journal of Antimicrobial Chemotherapy* (2000) 45, 9-13, The British Society for Antimicrobial Chemotherapy.
Cookson, Brad T., et al., "Identification of a Natural T Cell Epitope Presented by *Salmonella*-Infected Macrophages and Recognized by T Cells from Orally Immunized Mice," *The Journal of Immunology*, 1997, 158: 4310-4319, The American Association of Immunologists.
Curtiss, Roy III, et al., "*Salmonella typhimurium* Deletion Mutants Lacking Adenylate Cyclase and Cyclic AMP Receptor Protein Are Avirulent and Immunogenic," *Infection and Immunity*, Dec. 1987, p. 3035-3043, vol. 55, American Society for Microbiology.

(Continued)

*Primary Examiner*—Mark Navarro
(74) *Attorney, Agent, or Firm*—Thompson Coburn LLP

(57) ABSTRACT

The present invention relates to immunogenic compositions comprising a live attenuated derivative of a pathogenic Enterobacteriaceae bacteria. The attenuated derivative of a pathogenic Enterobacteriaceae bacteria comprises a polynucleotide that encodes a foreign antigen. The attenuated derivative of the pathogenic Enterobacteriaceae bacteria has increased expression of Type 1 fimbriae relative to the pathogenic Enterobacteriaceae bacteria from which the attenuated derivative was derived. The present invention also relates to immunogenic compositions that elicit an enhanced Th2 immune response in an individual. The present invention further provides a method of modulating the immune response of an individual comprising administering to said individual the immunogenic compositions of the present invention.

16 Claims, 11 Drawing Sheets

OTHER PUBLICATIONS

Datta, Dr. Naomi, et al., "Penicillinase Synthesis Controlled by Infections R Factors in Enterobacteriaceae," *Nature*, vol. 208, No. 5007, Oct. 1965, p. 239-241 No. 50076.

Del Prete, G., "Human Th1 and Th2 lymphocytes: their role in the pathophysiology of atopy," *Allergy* 1992: 47: 450-455.

Dong, Chen, et al., "Cell fate decision: T-helper 1 and 2 subsets in immune responses," *Arthritis Res* 2000, 2:179-188, Current Science Ltd.

Duguid, J.P., et al., "Fimbriae and Infectivity in *Salmonella typhimurium*," *J. Med. Microbiol.* vol. 9 (1976) p. 459-473.

Dunstan, Sarah J., et al., "Comparison of the Abilities of Different Attenuated *Salmonella typhimurium* Strains To Elicit Humoral Immune Response against a Heterologous Antigen," Infection and Immunity, Feb. 1998, p. 732-740, vol. 66, No. 2, American Society for Microbiology.

Eaves-Pyles, Tonyia D., et al., "Flagellin, a Novel Mediator of *Salmonella*-Induced Epithelial Activation and Systemic Inflammation: IκBα Degradation, Induction of Nitric Oxide Synthase, Induction of Proinflammatory Mediators, and Cardiovascular Dysfunction," *The Journal of Immunology*, 2001, 166: 1248-1260, The American Association of Immunologists.

Eaves-Pyles, Tonyia D., et al., "*Salmonella* Flagellin-Dependent Proinflammatory Responses Are Localized to the Conserved Amino and Carboxyl Regions of the Protein," *The Journal of Immunology*, 2001, 167: 7009-7016, The American Association of Immunologists.

Foster, John W. et al., "Acid-Sensitive Mutants of *Salmonella typhimurium* Identified through a Dinitrophenol Lethal Screening Strategy," *Journal of Bacteriology*, vol. 176, No. 9, May 1994, p. 2596-2602, American Society for Microbiology.

Fricker, Janet, "New vaccines: damming for multi-strain organisms?" *Drug Discovery Today*, vol. 7, No. 4, Feb. 2002, pp. 212-213, Elsevier Science Ltd.

Galán, Jorge E., et al., "Cloning and characterization of the *asd* gene of *Salmonella typhimurium*: use in stable maintenance of recombinant plasmids in *Salmonella* vaccine strains," *Gene*, 94 (1990) 29-35, Elsevier Science Publishers B.V. (Biomedical Division).

Galán, Jorge E., et al., "Virulence and vaccine potential pf *phoP* mutants of *Salmonella typhimurium*," *Microbial Pathogenesis* 1989; 6: 433-443, Academic Press Ltd.

Gay, P., et al., "Positive Selection Procedure for Entrapment of Insertion Sequence Elements in Gram-Negative Bacteria," *Journal of Bacteriology*, vol. 164, No. 2, Nov. 1985, p. 918-921, American Society for Microbiology.

Gentschev, Ivaylo, et al., "Development of antigen-delivery systems, based on the *Escherichia coli* hemolysin secretion pathway," *Gene—An International Journal on Genes and Genomes*, 179 (1996) 133-140, Elsevier Science V.V.

Gentschev, Ivo, et al., "Delivery of the p67 Sporozoite Antigen of *Theileria parva* by Using Recombinant *Salmonella dublin*: Secretion of the Product Enhances Specific Antibody Response in Cattle," *Infection and Immunity*, vol. 66, No. 5, May 1998, p. 2060-2064, American Society for Microbiology.

Gerwirtz, Andrew T., et al., "Cutting Edge: Bacterial Flagellin Activates Basolaterally Expressed TLR5 to Induce Epithelial Proinflammatory Gene Expression," *The Journal of Immunology*, 2001, pp. 1882-1885, The American Association of Immunologists.

Gerwirtz, Andrew T., et al., "*Salmonella typhimurium* translocates flagellin across intestinal epithelia, inducing a proinflammatory response," The Journal of Clinical Investigation, Jan. 2001, vol. 107, No. 1, pp. 99-109.

Greenwood, Brian, "The epidemiology of pneumococcal infection in children in the developing world," *Phil. Trans. R. Soc. Lond.* B (1999) 354, 777-785, The Royal Society.

Groisman, Eduardo A., et al., "*Salmonella typhimurium phoP* virulence gene is a transcriptional regulator," *Proc. Natl. Acad. Sci. USA*, vol. 86, pp. 7077-7081, Sep. 1989, Genetics.

Gulig, Paul A. et al., "Plasmid-Associated Virulence of *Salmonella typhimurium*," *Infection and Immunity*, vol. 55, No. 12, Dec. 1987, p. 2891-2901, American Society for Microbiology.

Gupta, Sudhir, et al., "Macrophage-T cell interaction in murine salmonellosis: selective down-regulation of ICAM-1 and B7 molecules in infect3ed macrophages and its probable role in cell-mediated immunity," *Eur. J. Immunol.* 1996, 26: 563-570, VCH Verlagsgesellschaft mbH, D-69451 Weinheim.

Hirschmann, J.V., "Use of the Pneumococcal Polysaccharide Vaccine Is Unwarranted in the U.S.," *ASM News*, vol. 66, No. 6, 2000, p. 326-327.

Hitchcock, Penny J. et al., "Morphological Heterogeneity Among *Salmonella* Lipopolysaccharide Chemotypes in Silver-Stained Polyacrylamide Gels," *Journal of Bacteriology*, vol. 154, No. 1, Apr. 1983, p. 269-277, American Society for Microbiology.

Hohmann, Elizabeth L., et al., "*phoP/phoQ*-Deleted *Salmonella typhi* (Ty800) Is a Safe and Immunogenic Single-Dose Typhoid Fever Vaccine in Volunteers," *The Journal of Infectious Diseases* 1996; 173: 1408-14, The University of Chicago.

Hollingshead, Susan K., et al., "Diversity of PspA: Mosaic Genes and Evidence for Past Recombination in *Streptococcus pneumoniae*," Infection and Immunity, vol. 68, No. 10, Oct. 2000, p. 5889-5900, American Society for Microbiology.

Husband, Alan J., "Novel vaccination strategies for the control of mucosal infection," *Vaccine*, vol. 11, Issue 2, 1993, pp. 107-112, Butterworth-Heinemann Ltd.

Jones, C. Hal, et al., "FimH adhesin of type 1 pili is assembled into a fibrillar tip structure in the *Enterobacteriaceae*;" *Proc. Natl. Acad. Sci.* USA vol. 92, No. 92, pp. 2081-2085, Mar. 1995, Biochemistry.

Kadonaga, James T., et al., "Signal Sequence Mutants of β-Lactamase," *The Journal of Biological Chemistry*, vol. 260, No. 30, Dec. 1985, pp. 16192-16199, The American Society of Biological Chemists, Inc., USA.

Kang, Ho Young, et al., "Transduction-Mediated Transfer of Unmarked Deletion and Point Mutations through Use of Counterselectable Suicide Vectors," *Journal of Bacteriology*, Jan. 2002, p. 307-312, vol. 184, No. 1, American Society for Microbiology.

Komoriya, Kaoru, et al., "Flagellar proteins and type III-exported virulence factors are the predominant proteins secreted into the culture media *Salmonella typhimurium*," *Molecular Microbiology* (1999) 34(4), 767-779, Blackwell Science Ltd.

Koshland, Douglas, et al., "Secretion of Beta-Lactamase Requires the Carboxy End of the Protein," *Cell*, vol. 20, 749-760, Jul. 1980, MIT.

Kyd, Jennelle M. et al., "Killed whole bacterial cells, a mucosal delivery system for the induction of immunity in the respiratory tract and middle ear: an overview," *Vaccine* 17 (1999) 1775-1781, Elsevier Science Ltd.

Langermann, Solomon, et al., "Systemic and mucosal immunity induced by BCG vector expressing outer-surface protein A of *Borrelia burgdorferi*," Nature, vol. 372, 1994, pp. 552-555.

Lee, Ming Hsun, et al., "Expression of *Helicobacter pylori* urease subunit B gene in *Lactococcus lactis* MG1363 and its use as a vaccine delivery system against *H. pylori* infection in mice", Vaccine 19 (2001) 3927-3935; Elsevier Science Ltd.

Lennox, E.S., "Transduction of Linked Genetic Characters of the Host by Bacterionhage P1," Virolgy 1, 190-206 (1955), Academic Press, San Diego, CA, USA.

Liaudet, Lucas, et al., "Comparison of Inflammation, Organ Damage, and Oxidant Stress Induced by *Salmonella enterica* Serovar Muenchen Flagellin and Serovar Enteritidis Lipopolysaccharide," *Infection and Immunity*, Jan. 2002, p. 192-198, vol. 70, No. 1, American Society for Microbiology.

Lockman, Hank A., et al., "Isolation and characterization of conditional adherent and non-type 1 fimbriated *Salmonella typhimurium* mutants," *Molecular Microbiology* (1992) 6(7), 933-945.

Lockman, Hank A., et al., "Virulence of Non-Type 1-Fimbriated and Nonfimbriated Nonflagellated *Salmonella typhimurium* Mutants in Murine Typoid Fever," *Infection and Immunity*, Feb. 1992, p. 491-496, vol. 60, No. 2, American Society for Microbiology.

Lo-Man, Richard, et al., "Extending the CD4[+] T-Cell Epitope Specificity of the Th1 Immune Response to an Antigen Using a *Salmonella enterica* Serovar Typhimurium Delivery Vehicle,"

*Infection and Immunity*, vol. 68, No. 6, Jun. 2000, p. 3079-3089, American Society for Microbiology.

Mathers, Kate, MSC, et al., "Antibody response to outer membrane proteins of *Moraxella catarrhalis* in children with otitis media," *The Pediatric Infectious Disease Journal*, vol. 18(11), Nov. 1999, pp. 982-988, Lippincott Williams & Wilkins, Inc.

McDaniel, Larry S., et al., "Comparison of the PspA Sequence from *Streptococcus pneumoniae* EF5668 to the Previously Identified PspA Sequence from Strain Rx1 and Ability of PspA from EF5668 To Elicit Protection against Pneumococci of Different Capsular Types", *Infection and Immunity*, Oct. 1998, 4748-4754, vol. 66, No. 10; American Society for Microbiology.

McDaniel, Larry S., et al., "Monoclonal Antibodies Against Protease-Sensitive Pneumococcal Antigens Can Protect Mice From Fatal Infection With *Streptococcus pneumoniae*," *J. Exp. Med.*, vol. 160, Aug. 1984, p. 386-397, The Rockefeller University Press.

McDermott, Patrick F., et al., "High-Affinity Interaction between Gram-Negative Flagellin and a Cell Surface Polypeptide Results in Human Monocyte Activation," *Infection and Immunity*, Oct. 2000, p. 5525-5529, vol. 68, No. 10, American Society for Microbiology.

McGhee, Jerry R., et al., "New Perspectives in Vaccine Development: Mucosal Immunity to Infections," *Infectious Agents and Disease* 2:55-73, 1993 Raven Press, Ltd., New York.

McSorley, Stephen J., et al., "Characterization of CD4+ T Cell Responses During Natural Infection with *Salmonella typhimurium*," *The Journal of Immunology*, 2000, p. 986-993, The American Association of Immunologists.

Medina, Eva, et al., "Pathogenicity Island 2 Mutants of *Salmonella typhimurium* Are Efficient Carriers for Heterologous Antigens and Enable Modulation of Immune Responses," *Infrection and Immunity*, Mar. 1999, p. 1093-1099, vol. 67, No. 3, American Society for Microbiology.

Medina, Eva, et al., "Use of live bacterial vaccine vectors for antigen delivery: potential and limitations," *Vaccine*, vol. 19 (2001) p. 1573-1580, Elsevier Science Ltd.

Mestecky, Jiri et al., "Prospects for human mucosal vaccines," *Genetically Engineered Vaccines*, Edited by J.E. Ciardi et al., Plenum Press, New York, 1992, pp. 13-23.

Miller, Samuel I., et al., "A two-component regulatory system (*phoP phoQ*) controls *Salmonella typhimurium* virulence," *Proc. Natl Acad. Sci. USA*, vol. 86, pp. 5054-5058, Jul. 1989, Genetics.

Mufson, Maurice A., "*Streptococcus pneumoniae*," Chapter 178, p. 1539-1550, Principles and Practice of Infectious Diseases, 3rd Edition, Churchill Livingstone, 1990.

Nakayama, Koji, et al., "Construction of an ASD+ Expression-Cloning Vector: Stable Maintenance and High Level Expression of Cloned Genes in a *Salmonella* Vaccine Strain," *Biotechnology*, vol. 6, Jun. 1988, p. 693-697.

Nayak, Arniya R., et al., "A Live Recombinant Avirulent Oral *Salmonella* Vaccine Expressing Pneumococcal Surface Protein A Induces Protective Responses against *Streptococcus pneumoniae*," *Infection and Immunity*, Aug. 1998, vol. 66, No. 8, p. 3744-3751, American Society for Microbiology.

Nicolle, L.E., et al., "Immunoblot Analysis of Serologic Response to Outer Membrane Proteins of *Escherichia coli* in Elderly Individuals with Urinay Tract Infections," *Journal of Clinical Microbiology*, vol. 26, No. 10, Oct. 1988, p. 2087-2091, American Society for Microbiology.

Niedergang, Florence, et al., "Entry and survival of *Salmonella typhimurium* in dendritic cells and presentation of recombinant antigens do not require macrophage-specific virulence factors," *PNAS*, Dec. 2000, vol. 97, No. 26 p. 14650-14655.

O'Garra, Anne et al., "The molecular basis of T helper 1 and T helper 2 cell differentiation," *Trends in Cell Biology* (vol. 10) Dec. 2000, p. 542-550, Elsevier Science Ltd.

Ogra, Pearay L., et al., *Mucosal Immunology*, Second Edition, 1999, 1994 by Academic Press, United States of America.

Ogushi, Ken-ichi, et al., "*Salmonella enteritidis* FliC (Flagella Filament Protein) Induces Human β -Defensin-2 mRNA Production by Caco-2 Cells," *The Journal of Biological Chemistry* vol. 276, No. 32, Aug. 2001, pp. 30521-30526, USA.

Okahashi, Nobuo, et al., "Oral Immunization of Interleukin-4 (IL-4) Knockout Mice with a Recombinant *Salmonella* Strain or Cholera Toxin Reveals that CD4+ Th2 Cells Producing IL-6 and IL-10 Are Associated with Mucosal Immunoglobulin A Responses," *Infection and Immunity*, vol. 64, No. 5, May 1996, p. 1516-1525, American Society for Microbiology.

Parker, Craig T., et al, "Contribution of flagella and Invasion proteins to pathogenesis of *Salmonella enterica* serovar enteritidis in checks," *FEMS Microbiology Letters*, 204 (2001) 287-291, Elsevier Science B.V.

Pascual, David W., et al., "Expression of Recombinant Enterotoxigenic *Escherichia coli* Colonization Factor Antigen I by *Salmonella typhimurium* Elicits a Biphasic T Helper Cell Response," *Infection and Immunity*, Dec. 1999, p. 6249-6256, vol. 67, No. 12, American Society for Microbiology.

Pawelek, John M., et al., "Tumor-targeted *Salmonella* as a Novel Anticancer Vector," Cancer Research 57, p. 4537-4544, Oct. 15, 1997.

Plückthun, Andreas, et al., "The Consequences of Stepwise Deletions from the Signal-processing Sit of β-Lactamase," *The Journal of Biological Chemistry*, vol. 262, No. 9, Mar. 25, 1987, pp. 3951-3957, The American Society of Biological Chemists, Inc., United States of America.

Raupach, Bärbel, et al., "Bacterial virulence, proinflammatory cytokines and host immunity: how to choose the appropriate *Salmonella* vaccine strain?" *Microbes and Infection*, 3, 2001, 1261-1269, Elsevier SAS.

Robertson, J.M.C., et al., "Adhesion of *Salmonella* enterica var Enteritidis strains lacking fimbriae and flagella to rat ileal explants cultured at the air interface or submerged in tissue culture medium," *J. Med. Microbiol.* vol. 49 (2000) 691-696, The Pathological Society of Great Britain and Ireland.

Robinson, Karen, et al., "Oral vaccination of mice against tetanus with recombinant *Lactococcus lactis*," Nature Biotechnology, vol. 15, Jul. 1997, 653-657.

Roland, Kenneth, et al., "Construction and Evaluation of a Δcya Δcrp *Salmonella typhimurium* Strain Expressing Avian Pathogenic *Escherichia coli* O78 LPS as a Vaccine to Prevent Airsacculitis in Chickens," Avian Diseases 43:429-441, 1999.

Rush, Catherine M., "Lactobacilli: vehicles for antigen delivery to the female urogenital tract," *Advances in Mucosal Immunology*, edited by J. Mestecky et al., Plenum Press, New York, 1995, pp. 15471552.

Sambrook, J., et al., *Molecular Cloning, A Laboratory Manual*, 2nd Edition, 1989, Cold Spring Harbor Laboratory Press.

Sbrogio-Almeida, M.E., et al., "Flagellin expressed by live *Salmonella* vaccine strains induces distinct antibody responses following delivery via systemic or mucosal immunization routes," *FEMS Immunology and Medical Microbiology* 30 (2001) 203-208, Elsevier Science B.V.

Schmieger, Horst, et al., "Altered Cotransduction Frequencies Exhibited by HT-Mutants of *Salmonella*-Phage P22," Molec. Gen. Genet. 143, 307-309 (1976), Springer-Verlag.

Schmitt, Clare K., et al., "Absence of All Components of the Flagellar Export and Synthesis Machinery Differentially Alters Virulence of *Salmonella enterica* Serovar Typhimurium in Models of Typhoid Fever, Survival in Macrophages, Tissue Culture Invasiveness, and Calf Enterocolitis," *Infection and Immunology*, Sep. 2001, p. 5619-5625, vol. 69, No. 9, American Society for Microbiology.

Schödel, Florian, et al., "Hybrid Hepatitis B Virus Core-Pre-S Proteins Synthesized in Avirulent *Salmonella typhmurium* and *Salmonella typhi* for Oral Vaccination," *Infection and Immunity*, May 1994, p. 1669-1676, American Society for Microbiology.

Shapiro, Eugene D., M.D., et al., "The Protective Efficacy of Poloyvalent Pneumococcal Polysaccharide Vaccine," *The New England Journal of Medicine*, vol. 325, No. 21, 1991, pp. 1453-1460, Massachusetts Medical Society.

Shaw, D.M., et al., "Engineering the microflora to vaccinate the mucosa: serum immunoglobulin G responses and activated draining cervical lymph nodes following mucosal application of tetanus toxin fragment C-expressing lactobacilli," *Immunology* 2000 100, 510-518, Blackwell Science Ltd.

Shinefield, Henry R., M.D., et al., "Safety and immunogenicity of heptabalent pneumococcal $CRM_{197}$ conjugate vaccine in infants and toddlers," *The Pediatric Infectious Disease Journal*, vol. 18(9), Sep. 1999, p. 757-763, Lippincott Williams & Wilkins, Inc.

Singh, Shiva P., et al., "Structural Relatedness of Enteric Bacterial Porins Assessed with Monoclonal Antibodies to *Salmonella typhimurium* OmpD and OmpC," *Journal of Bacteriology*, Mar. 1992, p. 1965-1973, American Society for Microbiology.

Sizemore, Donata R., et al., "Attenuated bacteria as a DNA delivery vehicle for DNA-mediated immunization," *Vaccine*, vol. 15, No. 8, pp. 804-807, 1997, Elsevier Science, Ltd., Great Britain.

Spellberg, Brad, et al., "Type 1/Type 2 Immunity in Infectious Diseases," *Clinical Infectious Diseases* 2001:32, pp. 76-102.

Sternberg, Nat L., et al., "Bacteriophage-Mediated Generalized Transduction in *Escherichia coli* and *Salmonella typhimurium*," *Methods In Enzymology*, vol. 204, pp. 18-43, 1991 Academic Press.

Su, Guo-fu, et al., "Extracellular export of Shiga toxin B-subunit/haemolysin A (C-terminus) fusion protein expressed in *Salmonella typhimurium aro*A-mutant and stimulation of B-subunit specific antibody responses in mice," *Microbial Pathogenesis*, 1992; 13: 465-476, Academic Press Ltd.

Summers, Richard G., et al., "Illicit Secretion of a Cytoplasmic Protein into the Periplasm of *Escherichia coli* Requires a Signal Peptide Plus a Portion of the Cognate Secreted Protein," *The Journal of Biological Chemistry*, vol. 264, No. 33, Issue of Nov. 25, pp. 20074-20081, 1989, printed in the U.S.A., The American Society of Biochemistry and Molecular Biology, Inc.

Tacket, Carol O., et al., "Comparison of the Safety and Immunogenicity of ΔcyaC ΔcrpD and Δcya Δcrp *Salmonella typhi* Strains in Adult Volunteers," *Infection and Immunity*, Feb. 1992, p. 536-541, vol. 60, No. 2, American Society for Microbiology.

Talkington, Deborah F., et al., "Analysis of pneumococcal PspA microheterogeneity in SDS polyacrylamide gels and the association of PspA with the cell membrane," *Microbial Pathogenesis* 1992; 13: 343-355, Academic Press Ltd.

Thole, Jelle ER, et al., "Live bacterial delivery systems for development of mucosal vaccines," *Molecular Therapeutics* 2000 2(1): 94-99, PharmaPress Ltd ISSN 1464-8431.

Tinker, Juliette K., et al., "FimW Is a Negative Regulator Affecting Type 1 Fimbrial Expression in *Salmonella enterica* Serovar Typhimurium," *Journal of Bacteriology*, Jan. 2001, p. 435-442, vol. 183, No. 2, American Society for Microbiology.

Townsend, Stacy M., et al., "*Salmonella enterica* Serovar Typhi Possesses a Unique Repertoire of Fimbrial Gene Sequences," *Infection and Immunity*, May 2001, p. 2894-2901, vol. 69-No. 5, American Society for Microbiology.

Van Den Dobbelsteen, Germie P.J.M., et al., "Mucosal immune responses to pneumococcal polysaccharides: implications for vaccination," *Trends In Microbiology*, vol. 3, No. 4, Apr. 1995, pp. 155-159, Elsevier Science Ltd.

Van Der Velden, Adrianus W.M., et al., "Multiple Fimbrial Adhesins Are Required for Full Virulence of *Salmonella typhimurium* in Mice," *Infection and Immunity*, Jun. 1998, p. 2803-2808, vol. 66, No. 6, American Society for Microbiology.

VanCott, John L., et al., "Regulation of host immune responses by modification of *Salmonella* virulence genes," *Nature Medicine*, vol. 4, No. 11, Nov. 1998, pp. 1247-1252, Nature America, Inc.

Velge-Roussel, F., et al., "Intranasal Immunization with *Toxoplasma gondii* SAG1 Induces Protective Cells into Both NALT and GALT Compartments," *Infection and Immunity*, Feb. 2000, p. 969-972, vol. 68, No. 2, American Society for Microbiology.

Verdugo-Rodriguez, A., et al., Detection of Antibodies against *Salmonella typhi* Outer Membrane Protein (OMP) Preparation in Typhoid Fever Patients, *Asian Pacific Journal of Allergy and Immunology* (1993) 11 : 45-52.

Wells, J.M., et al., "Lactic acid bacteria as vaccine delivery vehicles," *Antonie van Leeuwenhoek* 70: 317-330, 1996; Kluwer Academic Publishers, Netherlands.

Witholt, Bernard, et al., "An Efficient and Reproducible Procedure for the Formation of Spheroplasts from Variously Grown *Excherichia coli*," *Analytical Biochemistry* 74, 160-170 (1976), Academic Press, Inc.

Wyant, Timothy L., et al., "Potent Immunoregulatory Effects of *Salmonella typhi* Flagella on Antigenic Stimulation of Human Peripheral Blood Mononuclear Cells," *Infection and Immunity*, Mar. 1999, 1338-1346, vol. 67, No. 3, American Society for Microbiology.

Wyant, Timothy L., et al., "*Salmonella typhi* Flagella Are Potent Inducers of Proinflammatory Cytokine Secretion by Human Moncytes," *Infection and Immunity*, Jul. 1999, p. 3619-3625, vol. 67, No. 7, American Society for Microbiology.

Yamamoto, Massfumi, et al., "Oral Immunization with PspA Elicits Protective Humoral Immunity against *Stretococus pneumoniae* Infection," *Infection and Immunity*, Feb. 1997, p. 640-644, vol. 65, No. 2, American Society for Microbiology.

Zhang, Xin, et al., "Characterization and Immunogenicity of *Salmonella typhimurium* SL1344 and UK-1 Δcrp and Δcdt Deltion Mutants," *Infection and Immunity*, Dec. 1997, p. 5381-5387, vol. 65, No. 12, American Society for Microbiology.

Curtiss et al., Strategies for the use of live recombinant avirulent bacterial vaccines for mucosal immunization, Essentials of Mucosal Immunology, 1996, Academic Press, San Diego, CA.

Curtiss, Bacterial infectious disease control by vaccine development, J. Clin. Invest., Oct. 2002;110(8): pp. 1061-1066.

Galan et al., Molecular and Cellular Bases of Salmonella and Shigella Interactions with Host Cells, Cellular and Molecular Biology, 1996, vol. 2, pp. 2757-2773, ASM Press, Washington DC.

Isaacson et al., In vitro adhesion of *Escherichia coli* to porcine small intestinal epithelial cells: pili as adhesive factors, Infect. Immun., Aug. 1978;21(2): pp. 392-397.

Schifferli et al., Genetic analysis of 987P adhesion and fimbriation of *Escherichia coli*: the fas genes link both phenotypes, J. Bacteriol., Feb. 1991;173(3): pp. 1230-1240.

\* cited by examiner

FIGURE 3. PspA specific IgG1 and IgG2a responses by live *S. typhimurium* Vaccines with different types of attenuation FIGURE 4. Construction of suicide vector for ΔfimA2119

PRIMER 1: FimA-L-KpnI
5' GG G GTA CC C GAA GAC CTG CTG CGA C 3'

PRIMER 2: FimA-L-EcoRI
5' CC G AAT TC A ATT ACA CAC ACC CGG T 3'

PRIMER 3: FimA-R-EcoRI
5' CC G AAT TC A TCC CGT CAG GGA ACG G 3'

PRIMER 4: FimA-R-SacI
5' GC G AGC TC A TTT GCC GCT GCT GGT C 3'

FIGURE 5. Construction of suicide vector for ΔfimH1019

PRIMER 5: FimH-L-KpnI
5' GG G GTA CC T GGC AAC TTT CCG GCG G 3'

PRIMER 6: FimH-L-EcoRI
5' CC G AAT TC C TTT TAT GAC GCC GGA C 3'

PRIMER 7: FimH-R-EcoRI
5' CC G AAT TC T TAT GAT TAA GGA GGC A 3'

PRIMER 8: FimH-R-SacI
5' GC G AGC TC G CGA TAT AGT TCG CAT A 3'

FIGURE 6. Construction of suicide vector for ΔfimW113

FIGURE 7.
A. ΔfimA2119
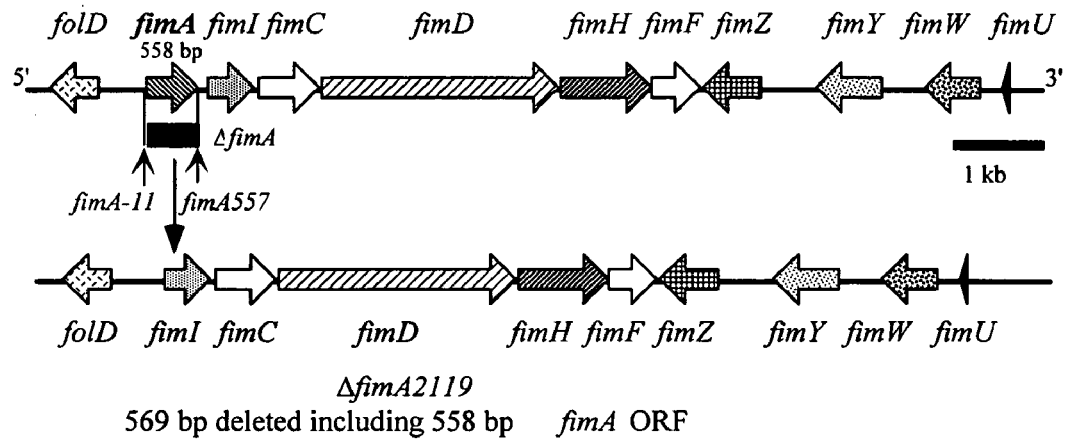
ΔfimA2119
569 bp deleted including 558 bp *fimA* ORF
B. ΔfimH1019
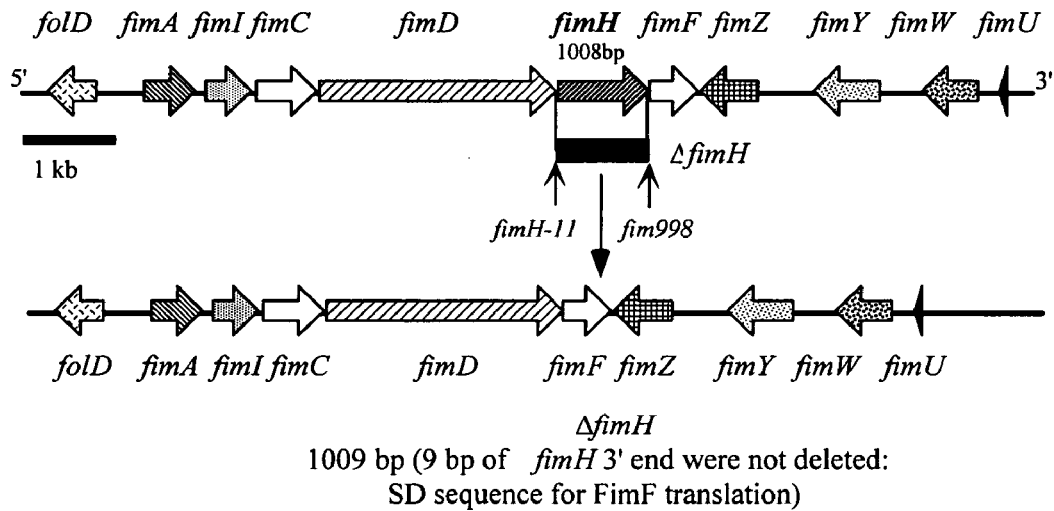
ΔfimH
1009 bp (9 bp of *fimH* 3' end were not deleted:
SD sequence for FimF translation)
C. ΔfimW113
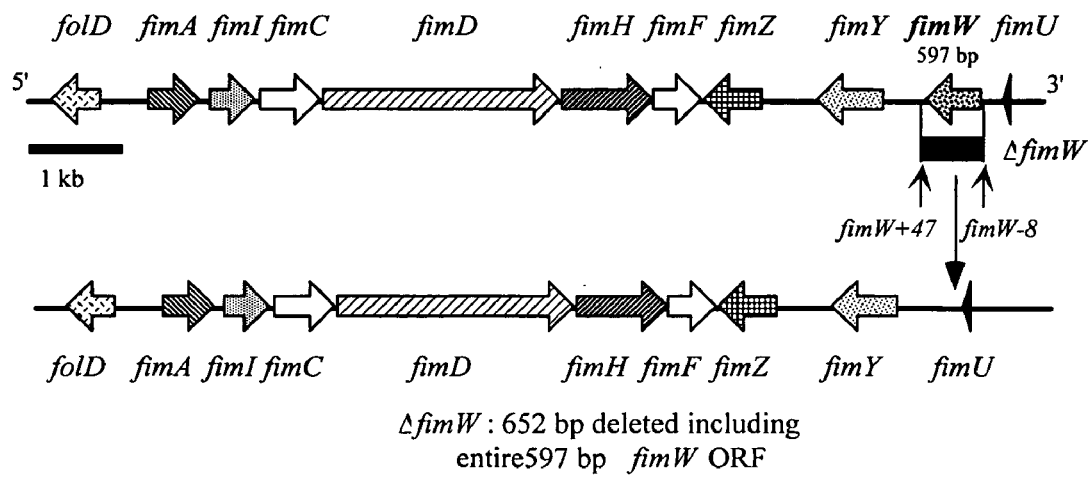
ΔfimW : 652 bp deleted including
entire 597 bp *fimW* ORF Figure 8. Construction of suicide vector for ΔfliC825
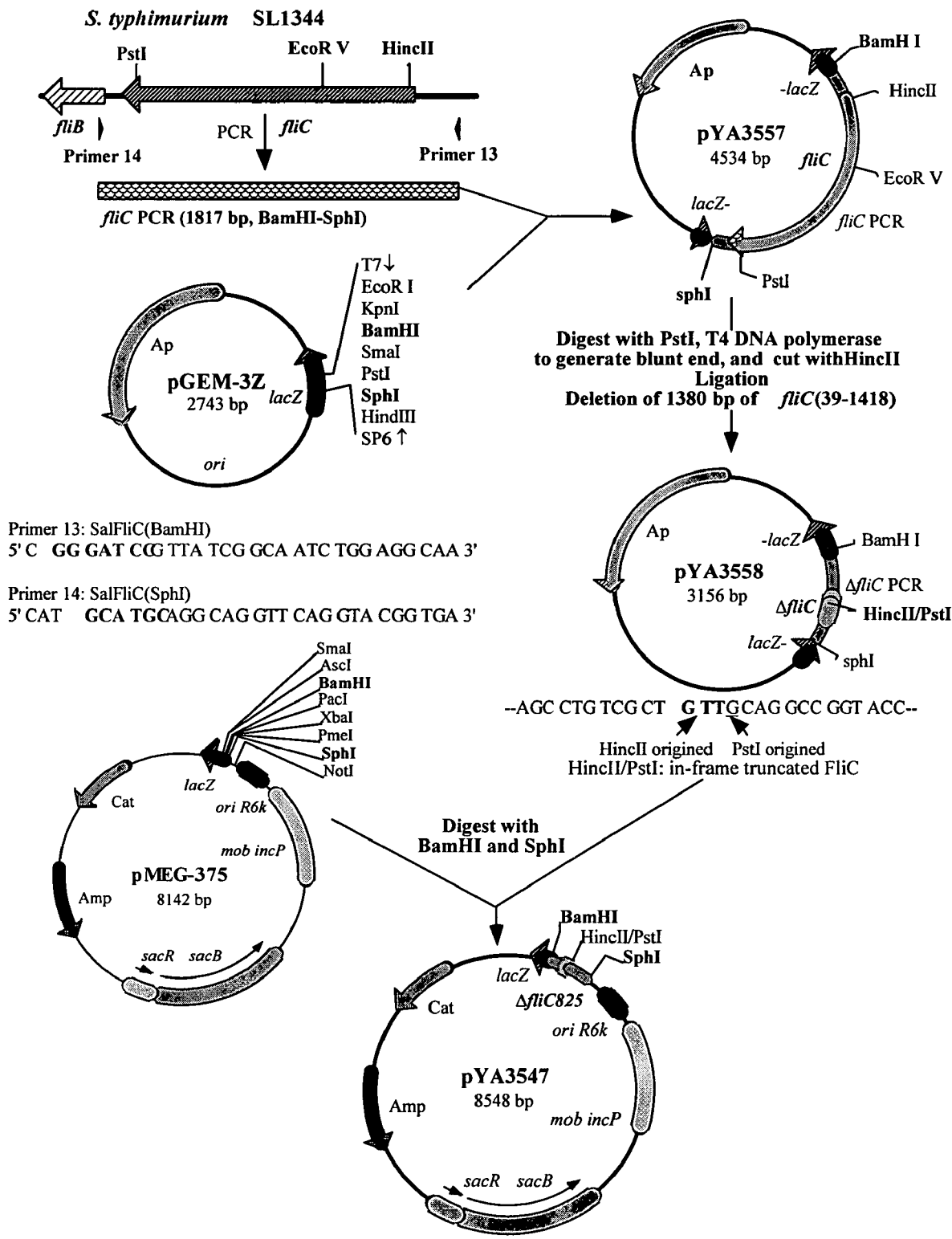

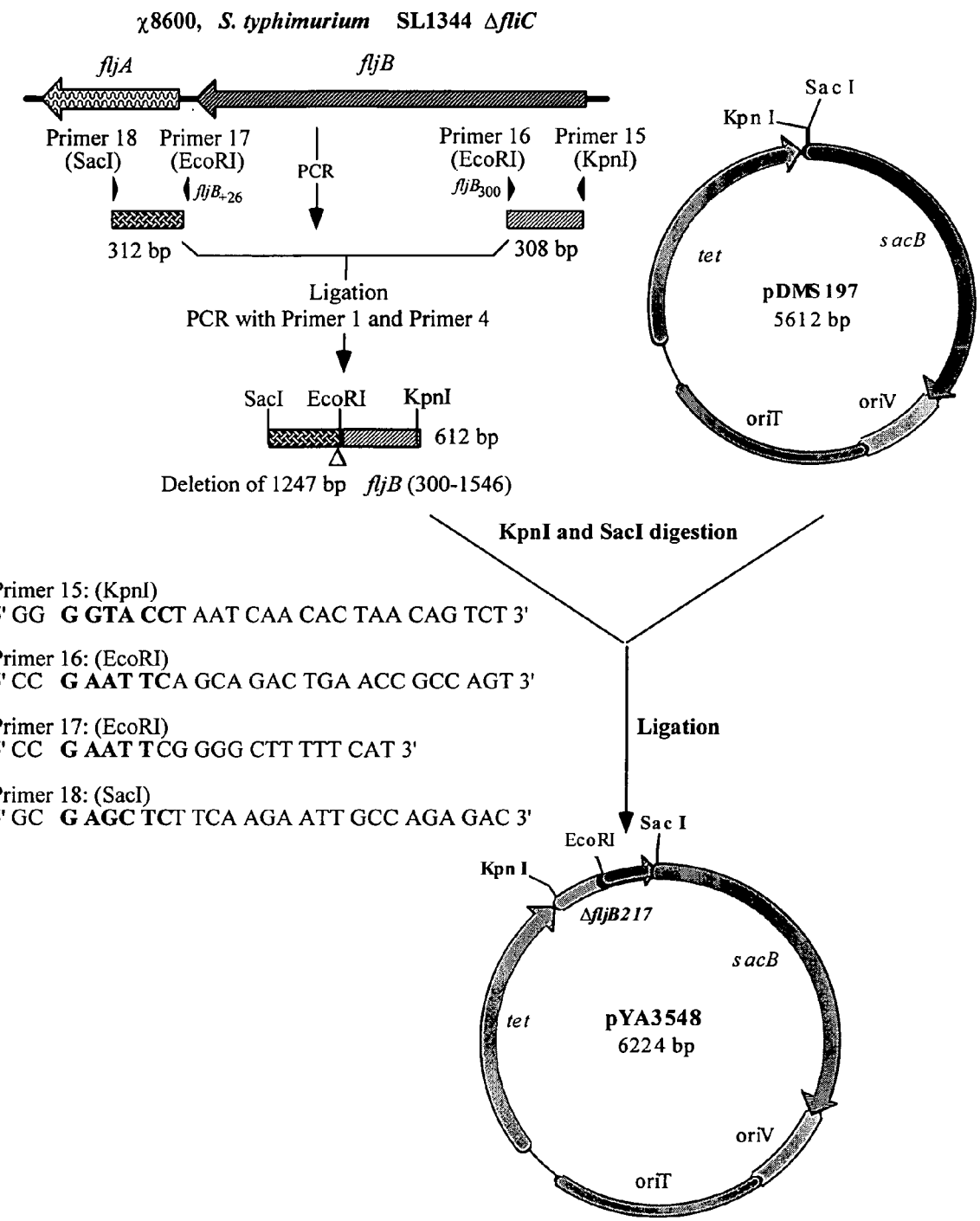
FIGURE 9 Construction of suicide vector for ΔfljB217

FIGURE 10. *Salmonella typhimurium* SL1344 chromosomal deletions:
A. Δ*fliC825*
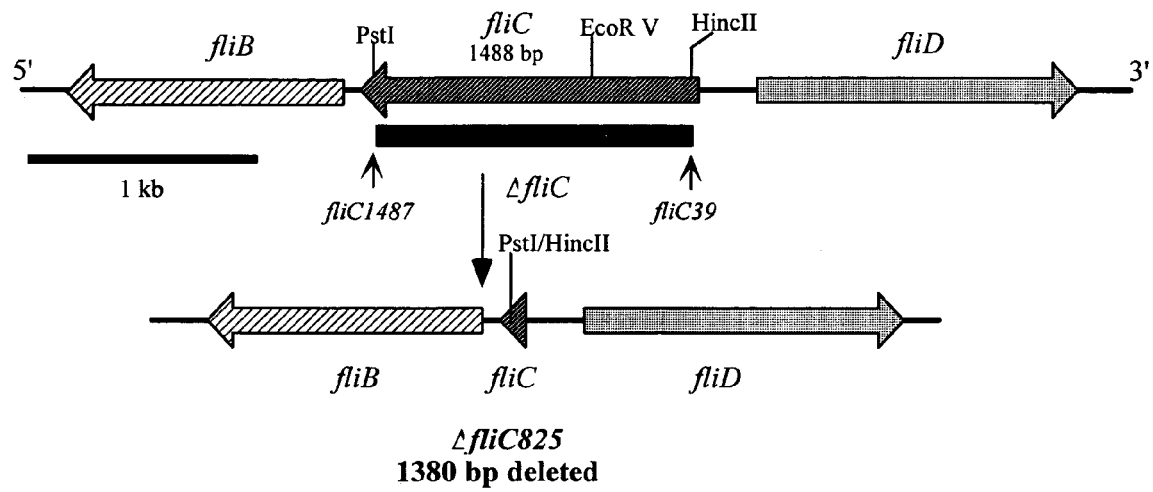
Δ*fliC825*
1380 bp deleted
B. Δ*fljB217*
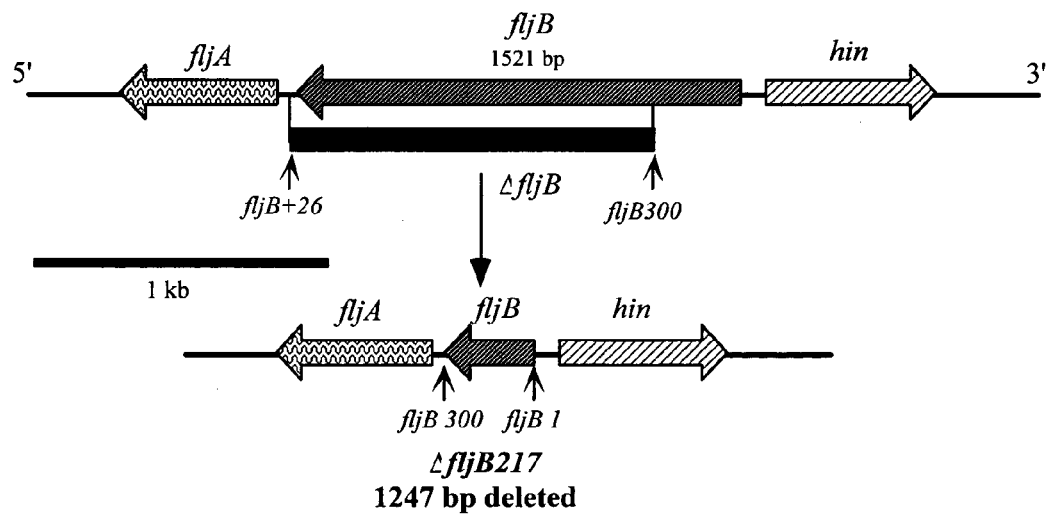
Δ*fljB217*
1247 bp deleted

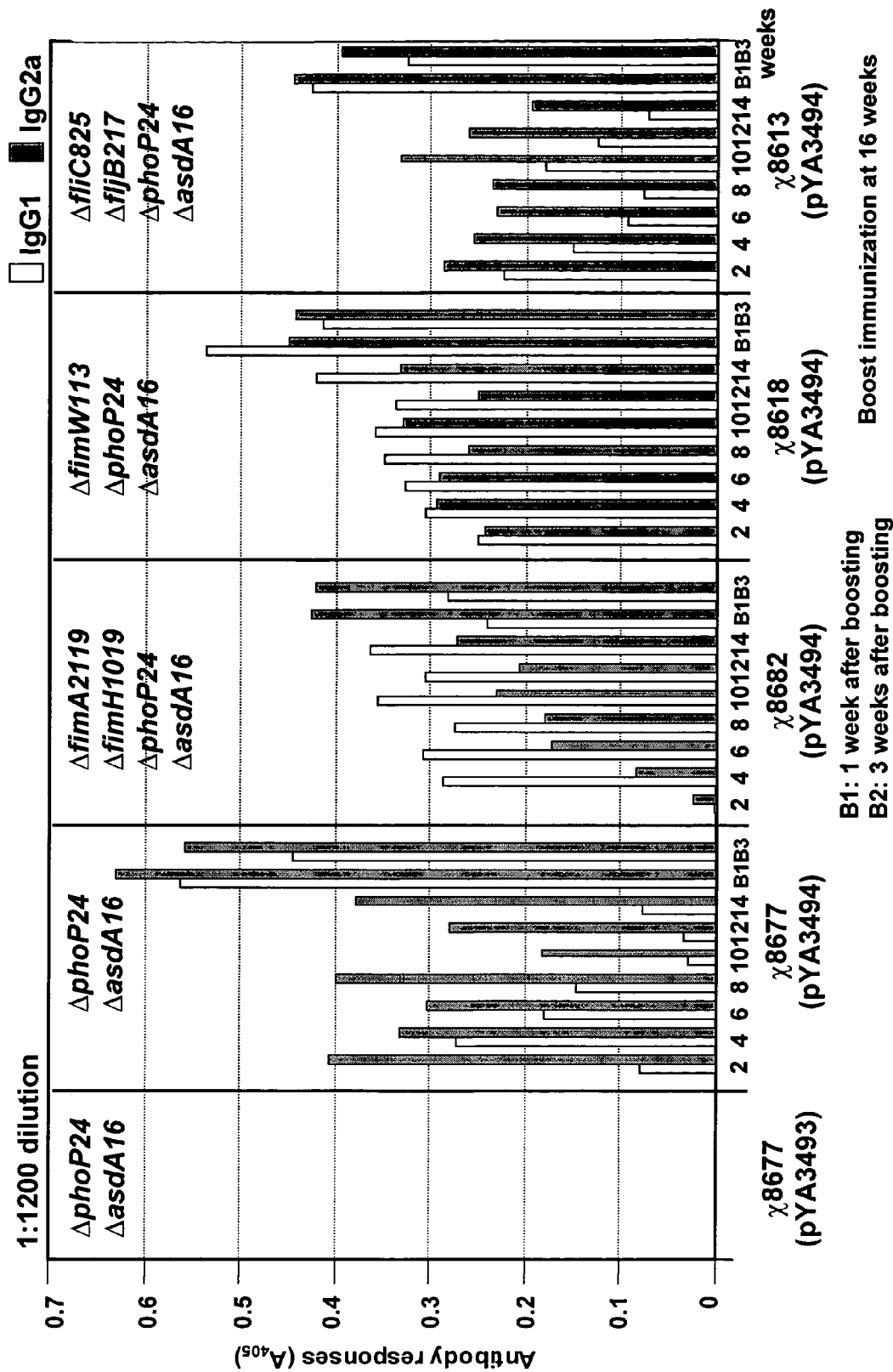
FIGURE 11. PspA specific IgG1 and IgG2a responses induced by live S. typhimurium vaccines with various adhesion mutants

SEQUENCE LISTING

<160> NUMBER OF SEQ ID NOS: 22

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 1
ggggtacccg aagacctgct gcgac                                              25

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 2
ccgaattcaa ttacacacac ccggt                                              25

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 3
ccgaattcat cccgtcaggg aacgg                                              25

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 4
gcgagctcat ttgccgctgc tggtc                                              25

<210> SEQ ID NO 5
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 5
ggggtacctg gcaactttcc ggcgg                                              25

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 6
ccgaattcct tttatgacgc cggac                                              25

<210> SEQ ID NO 7
<211> LENGTH: 25

```
<212> TYPE: DNA
<213> ORGANISM: Artificial Sequence
<220> FEATURE:
<223> OTHER INFORMATION: Description of Artificial Sequence: Primer

<400> SEQUENCE: 7
ccgaattctt atgattaagg aggca                                              25

<210> SEQ ID NO 8
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 8
gcgagctcgc gatatagttc gcata                                              25

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 9
ggcggatcct gtcatctaat gagcggaat                                          29

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 10
gccgaattca agtaacgata cctacaggc                                          29

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 11
cgcgaattca tcctacacgg caggtgaat                                          29

<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence: Primer

<400> SEQUENCE: 12
ccgaagcttt cactgcaacc atgaatgac                                          29

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 13
```
cgggatccgt tatcggcaat ctggaggcaa                                    30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 14
catgcatgca ggcaggttca ggtacggtga                                    30

<210> SEQ ID NO 15
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 15
ggggtaccta atcaacacta acagtct                                       27

<210> SEQ ID NO 16
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 16
ccgaattcag cagactgaac cgccagt                                       27

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 17
ccgaattcgg ggcttttca t                                              21

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 18
gcgagctctt caagaattgc cagagac                                       27

<210> SEQ ID NO 19
<211> LENGTH: 230
<212> TYPE: PRT
<213> ORGANISM: Streptococcus pneumoniae

<400> SEQUENCE: 19

Leu Gln Ala Ser Asn Glu Ser Gln Arg Lys Glu Ala Asp Lys Lys Ile
 1               5                  10                  15

Lys Glu Ala Thr Gln Arg Lys Asp Glu Ala Glu Ala Phe Ala Thr
            20                  25                  30

Ile Arg Thr Thr Ile Val Val Pro Glu Pro Ser Glu Leu Ala Glu Thr
        35                  40                  45

-continued

```
Lys Lys Lys Ala Glu Glu Ala Thr Lys Glu Ala Glu Val Ala Lys Lys
 50                  55                  60

Lys Ser Glu Glu Ala Ala Lys Glu Val Glu Val Glu Lys Asn Lys Ile
 65                  70                  75                  80

Leu Glu Gln Asp Ala Glu Asn Glu Lys Lys Ile Asp Val Leu Gln Asn
                 85                  90                  95

Lys Val Ala Asp Leu Glu Lys Gly Ile Ala Pro Tyr Gln Asn Glu Val
            100                 105                 110

Ala Glu Leu Asn Lys Glu Ile Ala Arg Leu Gln Ser Asp Leu Lys Asp
            115                 120                 125

Ala Glu Glu Asn Asn Val Glu Asp Tyr Ile Lys Glu Gly Leu Glu Gln
            130                 135                 140

Ala Ile Thr Asn Lys Lys Ala Glu Leu Ala Thr Thr Gln Gln Asn Ile
145                 150                 155                 160

Asp Lys Thr Gln Lys Asp Leu Glu Asp Ala Glu Leu Glu Leu Glu Lys
                165                 170                 175

Val Leu Ala Thr Leu Asp Pro Glu Gly Lys Thr Gln Asp Glu Leu Asp
            180                 185                 190

Lys Glu Ala Ala Glu Ala Glu Leu Asn Glu Lys Val Glu Ala Leu Gln
            195                 200                 205

Asn Gln Val Ala Glu Leu Glu Glu Leu Ser Lys Leu Glu Asp Asn
            210                 215                 220

Leu Lys Asp Ala Glu Thr
225                 230
```

<210> SEQ ID NO 20
<211> LENGTH: 257
<212> TYPE: PRT
<213> ORGANISM: Streptococcus pneumoniae

<400> SEQUENCE: 20

```
Leu Gln Ser Pro Val Ala Ser Gln Ser Lys Ala Glu Lys Asp Tyr Asp
  1               5                  10                  15

Ala Ala Lys Lys Asp Ala Lys Asn Ala Lys Lys Ala Val Glu Asp Ala
             20                  25                  30

Gln Lys Ala Leu Asp Asp Ala Lys Ala Gln Lys Lys Tyr Asp Glu
             35                  40                  45

Asp Gln Lys Lys Thr Glu Glu Lys Ala Ala Leu Glu Lys Ala Ala Ser
 50                  55                  60

Glu Glu Met Asp Lys Ala Val Ala Val Gln Gln Ala Tyr Leu Ala
 65                  70                  75                  80

Tyr Gln Gln Ala Thr Asp Lys Ala Ala Asp Ala Ala Asp Lys Met
                 85                  90                  95

Ile Asp Glu Ala Lys Lys Arg Glu Glu Glu Ala Lys Thr Lys Phe Asn
            100                 105                 110

Thr Val Arg Ala Met Val Val Pro Glu Pro Gln Leu Ala Glu Thr
            115                 120                 125

Lys Lys Lys Ser Glu Glu Ala Lys Gln Lys Ala Pro Glu Leu Thr Lys
            130                 135                 140

Lys Leu Glu Glu Ala Lys Ala Lys Leu Glu Glu Ala Lys Lys Ala
145                 150                 155                 160

Thr Glu Ala Lys Gln Lys Val Asp Ala Glu Glu Val Ala Pro Gln Ala
                165                 170                 175

Lys Ile Ala Glu Leu Glu Asn Gln Val His Arg Leu Glu Gln Glu Leu
            180                 185                 190
```

Lys Glu Ile Asp Glu Ser Glu Ser Glu Asp Tyr Ala Lys Glu Gly Phe
            195                 200                 205

Arg Ala Pro Leu Gln Ser Lys Leu Asp Ala Lys Lys Ala Lys Leu Ser
    210                 215                 220

Lys Leu Glu Glu Leu Ser Asp Lys Ile Asp Glu Leu Asp Ala Glu Ile
225                 230                 235                 240

Ala Lys Leu Glu Asp Gln Leu Lys Ala Ala Glu Glu Asn Asn Asn Val
            245                 250                 255

Glu

<210> SEQ ID NO 21
<211> LENGTH: 487
<212> TYPE: PRT
<213> ORGANISM: Streptococcus pneumoniae

<400> SEQUENCE: 21

Leu Gln Ala Ser Asn Glu Ser Gln Arg Lys Glu Ala Asp Lys Lys Ile
1               5                   10                  15

Lys Glu Ala Thr Gln Arg Lys Asp Glu Ala Glu Ala Phe Ala Thr
            20                  25                  30

Ile Arg Thr Thr Ile Val Val Pro Glu Pro Ser Glu Leu Ala Glu Thr
        35                  40                  45

Lys Lys Lys Ala Glu Glu Ala Thr Lys Glu Ala Glu Val Ala Lys Lys
    50                  55                  60

Lys Ser Glu Glu Ala Ala Lys Glu Val Glu Val Glu Lys Asn Lys Ile
65                  70                  75                  80

Leu Glu Gln Asp Ala Glu Asn Glu Lys Lys Ile Asp Val Leu Gln Asn
                85                  90                  95

Lys Val Ala Asp Leu Glu Lys Gly Ile Ala Pro Tyr Gln Asn Glu Val
            100                 105                 110

Ala Glu Leu Asn Lys Glu Ile Ala Arg Leu Gln Ser Asp Leu Lys Asp
        115                 120                 125

Ala Glu Glu Asn Asn Val Glu Asp Tyr Ile Lys Glu Gly Leu Glu Gln
    130                 135                 140

Ala Ile Thr Asn Lys Lys Ala Glu Leu Ala Thr Thr Gln Gln Asn Ile
145                 150                 155                 160

Asp Lys Thr Gln Lys Asp Leu Glu Asp Ala Glu Leu Glu Leu Glu Lys
                165                 170                 175

Val Leu Ala Thr Leu Asp Pro Glu Gly Lys Thr Gln Asp Glu Leu Asp
            180                 185                 190

Lys Glu Ala Ala Glu Ala Glu Leu Asn Glu Lys Val Glu Ala Leu Gln
        195                 200                 205

Asn Gln Val Ala Glu Leu Glu Glu Leu Ser Lys Leu Glu Asp Asn
    210                 215                 220

Leu Lys Asp Ala Glu Thr Leu Gln Ser Pro Val Ala Ser Gln Ser Lys
225                 230                 235                 240

Ala Glu Lys Asp Tyr Asp Ala Ala Lys Lys Asp Ala Lys Asn Ala Lys
                245                 250                 255

Lys Ala Val Glu Asp Ala Gln Lys Ala Leu Asp Asp Lys Ala Ala
            260                 265                 270

Gln Lys Lys Tyr Asp Glu Asp Gln Lys Lys Thr Glu Glu Lys Ala Ala
        275                 280                 285

Leu Glu Lys Ala Ala Ser Glu Glu Met Asp Lys Ala Val Ala Ala Val
    290                 295                 300

```
Gln Gln Ala Tyr Leu Ala Tyr Gln Gln Ala Thr Asp Lys Ala Ala Lys
305                 310                 315                 320

Asp Ala Ala Asp Lys Met Ile Asp Glu Ala Lys Lys Arg Glu Glu Glu
                325                 330                 335

Ala Lys Thr Lys Phe Asn Thr Val Arg Ala Met Val Val Pro Glu Pro
                340                 345                 350

Glu Gln Leu Ala Glu Thr Lys Lys Lys Ser Glu Glu Ala Lys Gln Lys
            355                 360                 365

Ala Pro Glu Leu Thr Lys Lys Leu Glu Glu Ala Lys Ala Lys Leu Glu
    370                 375                 380

Glu Ala Glu Lys Lys Ala Thr Glu Ala Lys Gln Lys Val Asp Ala Glu
385                 390                 395                 400

Glu Val Ala Pro Gln Ala Lys Ile Ala Glu Leu Glu Asn Gln Val His
                405                 410                 415

Arg Leu Glu Gln Glu Leu Lys Glu Ile Asp Glu Ser Glu Ser Glu Asp
                420                 425                 430

Tyr Ala Lys Glu Gly Phe Arg Ala Pro Leu Gln Ser Lys Leu Asp Ala
            435                 440                 445

Lys Lys Ala Lys Leu Ser Lys Leu Glu Glu Leu Ser Asp Lys Ile Asp
    450                 455                 460

Glu Leu Asp Ala Glu Ile Ala Lys Leu Glu Asp Gln Leu Lys Ala Ala
465                 470                 475                 480

Glu Glu Asn Asn Asn Val Glu
                485

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agcctgtcgc tgttgcaggc cggtacc                                          27
```

MODULATION OF IMMUNE RESPONSES TO FOREIGN ANTIGENS EXPRESSED BY RECOMBINANT ATTENUATED BACTERIAL VECTORS

CROSS-REFERENCE TO RELATED APPLICATIONS

The present application claims priority to provisional application No. 60/372,676, filed on Apr. 15, 2002 and provisional application No. 60/373,669, filed on Apr. 18, 2002.

REFERENCE TO GOVERNMENT GRANT

This invention was made with government support under Grant No. AI24533 and/or Grant No. DE06669 by the National Institutes of Health. The government may have certain rights in the invention.

SEQUENCE LISTING

This application contains a paper copy of a Sequence Listing and appended hereto is a computer readable form of the same Sequence Listing, which is hereby incorporated by reference. The sequence listing information recorded in computer readable form is identical to the written sequence listing.

FIELD OF THE INVENTION

The invention relates generally to the field of recombinant attenuated bacteria, and more specifically to recombinant bacteria and methods for modulating the type of immune response induced by foreign antigens expressed by a carrier bacterial strain.

BACKGROUND OF THE INVENTION

Vaccination constitutes the most cost-effective tool for the prophylaxis of infectious diseases.

The elicitation of an efficient immune response at the mucosal level after immunization is highly desired. Among the approaches for triggering an efficient immune response, the use of attenuated enteropathogenic bacteria as carriers has received substantial attention. Attenuated strains of bacteria constructed by recombinant DNA technology have been developed as live vaccines for humans and other animals. For a recent review of the use of attenuated bacterial strains as antigen delivery vectors, see Medina and Guzman, *Vaccine* 19:1573-1580 (2001), which is hereby incorporated by reference along with the references cited therein. Examples of attenuated bacteria that have been successfully used as antigen delivery vectors include *Listeria monocytogenes*, *Salmonella* spp., *Vibrio cholera*, *Shigella* spp., *Mycobacterium bovis* BCG, *Yersinia enterocolitica*, *Bacillus anthracis*, *Streptococcus gordonii*, *Lactobaccillus* spp., *Staphylococcus* spp. and *E. coli*. Id. Such attenuated bacteria can stimulate mucosal and/or systemic immunity against the carrier itself or against heterologous antigens expressed by the carrier bacteria. See also, e.g., U.S. Pat. Nos. 6,024,961; 4,888,170; 5,389,368; 5,855,879; 5,855,880; 5,294,441; 5,468,485; 5,387,744; 5,840,483; 5,672,345; 5,424,065; 5,888,799; 5,656,488; 5,006,335; 5,643,771; 5,980,907; 5,851,519 and 5,527,529, describing attenuated bacterial strains suitable for use as vaccines, all of which are hereby incorporated by reference.

Th1 and Th2 cells exist in humans and other animals. Th1 cells are the principal regulators of type 1 immunity, while Th2 cells stimulate high titers of antibody. Clinically, a correlation has been established between antibody titer and efficacy of vaccines. Thus, a Th2 dominant immune response is highly desirable for certain vaccine applications. Achieving the correct balance between the different arms of the immune system when an immune response is elicited is an important factor bearing on the efficacy of a particular vaccine. Golding and Scott, 1995 *Ann NY Acad Sci*, 754: 126-137, Del Prete, B., 1992, *Allergy*, 47:450-455, Dong and Flavell, 2000, *Arthritis Res*, 2:179-188 and Spellberg and Edwards, 2001, *Clin Infect Dis*, 32:76-102 present recent reviews on Th1 and Th2 mediated immune responses.

Many factors have been shown to effect the polarization of Th0 cells into mature Th1 or Th2 cells. For example, the local cytokine environment, the presence of immunologically active hormones, the dose and route of antigen administration, and the type and characteristics of the antigen-presenting cell stimulating the T cell all can have an effect on the balance of Th1 versus Th2 type immune response that is elicited. Thus, it is conceivable that the immune response can be modulated by manipulating any one, or combination of these factors.

One area that has received considerable attention is altering the characteristics of the antigen presenting cell, or antigen carrier, in order to modulate the type of immune response elicited. Several studies have investigated the immune responses to heterologous antigens elicited by carrier bacteria strains that harbor mutations in various genes. Dunstan et al., 1998, *Infect and Immun*, 66:732-740; Medina et al., 1999, *Infect and Immun*, 67:1093-1099; VanCott et al., 1998, *Nature Medicine*, 4:1247-1252; Pascual et al., 1999, *Infect and Immun*, 67:6249-6256. The studies above confirm that different attenuating mutations and combinations of mutations are capable of eliciting immune responses with a differing balance of Th1 versus Th2 levels.

There remains a need for further research in the development of strategies to target appropriate helper T cell responses according to particular needs. Thus, the availability of carrier strains that are well characterized in terms of the particular immune response they elicit should enable fine tuning of the immune response triggered against heterologous or homologous antigens according to specific needs.

Related Art:

A. Fimbriae Related References:

1. Townsend, S. M., N. E. Kramer, R. Edwards, S. Hamlin, M. Simmonds, K. Stevens, S. Maloy, J. Parkhill, G. Dougan, and A. J. Baumler. 2001. *Salmonella enterica* serovar Typhi possesses a unique repertoire of fimbrial gene sequences. 2001. Infect. Immun. 69:2894-2901.
2. Tinker J. K., L. S. Hancox, and S. Clegg. FimW is a negative regulator affecting type 1 fimbrial expression in *Salmonella enterica* serovar typhimurium. 2001. J. Bacteriol. 183:435-432.
3. Robertson J. M., G. Grant, E. Allen-Vercoe, M. J. Woodward, A. Pusztai, and H. J. Flint. 2000. Adhesion of *Salmonella enterica* var Enteritidis strains lacking fimbriae and flagella to rat ileal explants cultured at the air interface or submerged in tissue culture medium. J. Med. Microbiol. 49:691-696.
4. van der Velden A. W., A. J. Baumler, R. M. Tsolis, and F. Heffron. 1998. Multiple fimbrial adhesins are required for full virulence of *Salmonella typhimurium* in mice. Infect. Immun. 66:2803-2808.

5. Baumler A. J., R. M. Tsolis, and F. Heffron. 1997. Fimbrial adhesins of *Salmonella typhimurium*. Role in bacterial interactions with epithelial cells. Adv. Exp. Med. Biol. 412:149-158.
6. Baumler A. J., R. M. Tsolis, and F. Heffron. 1996. Contribution of fimbrial operons to attachment to and invasion of epithelial cell lines by *Salmonella typhimurium*. Infect. Immun. 64:1862-1865.
7. Lockman H. A., and R. Curtiss III. 1992. Isolation and characterization of conditional adherent and non-type 1 fimbriated *Salmonella typhimurium* mutants. Mol. Microbiol. 6:933-945.
8. Lockman H. A., and R. Curtiss III. 1992. Virulence of non-type 1-fimbriated and nonflagellated *Salmonella typhimurium* mutants in murine typhoid fever. Infect. Immun. 60:491-496.
9. Duguid J. P., M. R. Darekar, and D. W. Wheater. 1976. Fimbriae and infectivity in *Salmonella typhimurium*. J. Med. Microbiol. 9:459-473.

B. Different Attenuation Type Related References:
10. Raupach B., and S. H. Kaufmann. 2001. Bacterial virulence, proinflammatory cytokines and host immunity: how to choose the appropriate *Salmonella* vaccine strain? Microbes. Infect. 3:1261-1269.
11. Niedergang F., J. C. Sirard, C. T. Blanc, and J. P. Kraehenbuhl. 2000. Entry and survival of *Salmonella typhimurium* in dendritic cells presentation of recombinant antigens do not require macrophage-specific virulence factors. Proc. Natl. Acad. Sci. USA 97:14650-14655.
12. VanCott J. L., S. N. Chatfield, M. Robert, D. M. Hone, E. L. Hohmann, D. W. Pascual, M. Yamamoto, H. Kiyono, and J. R. McGhee. 1998. Regulation of host immune responses by modification of *Salmonella* virulence genes. Nat. Med. 4:1247-1252.

C. Flagella Related References:
13. Liaudet L., K. G. Murthy, J. G Mabley, P. Pacher, F. G. Soriano, A. L. Salzman, and C. Szabo. 2002. Comparison of inflammation, organ damage, and oxidant stress induced by *Salmonella enterica* serovar Muenchen flagellin and serovar Enteritidis lipopolysaccharides. Infect. Immun. 70:192-198.
14. Eaves-Pyles T. D., H. R. Wong, K. Odoms, and R. B. Pyles. 2001. *Salmonella* flagellin-dependent proinflammatory responses are localized to the conserved amino and carboxyl regions of the protein. J. Immunol. 167:7009-7016.
15. Parker C. T., and J. Guard-Petter. 2001. Contribution of flagella and invasion protein to pathogenesis of *Salmonella enterica* serovar enteritidis in chicks. FEMS Microbiol. Lett. 204:287-291.
16. Schmitt C. K., J. S. Ikeda, S. C. Darnell, P. R. Watson, J. Bispham, T. S. Wallis, D. L. Weinstein, E. S. Metcalf, and A. D. O'Brien. 2001. Absence of all components of the flagellar export and synthesis machinery differentially alters virulence of *Salmonella enterica* serovar Typhimirium in models of typhoid fever, survival in macrophages, tissue culture invasiveness, and calf enterocolitis. Infect. Immun. 69:5619-5625.
17. Gewirtz A. T., T. A. Navas, S. Lyons, P. J. Godowski, and J. L. Madara. 2001. Cutting edge: bacterial flagellin activates basolaterally expressed TLR5 to induce epithelial proinflanmmatory gene expression J. Immunol. 167:1882-1885.
18. Ogushi K., A. Wada, T. Niidome, N. Mori, K. Oishi, T. Nagatake, A. Takahashi, H. Asakura, S. Makino, H. Hojo, Y. Nakahara, M. Ohsaki, T. Hatakeyama, H. Aoyagi, H. Kurazono, J. Moss, and T. Hirayama. 2001. *Salmonella enteritidis* FliC (flagella filament protein) induces human beta-defensin-2 mRNA production by Caco-2 cells. J. Biol. Chem. 276:30521-30526.
19. Sbrogio-Almeida M. E., and L. C. Ferreira. 2001. Flagellin expressed by live *Salmonella* vaccine strains induces distinct antibody responses following delivery via systemic or mucosal immunization routes. FEMS Immunol. Med. Microbiol. 30:203-208.
20. Eaves-Pyles T., K. Murthy, L. Liaudet, L. Virag, G. Ross, F. G. Soriano, C. Szabo, and A. L. Salzman. 2001. Flagellin, a novel mediator of *Salmonella*-induced epithelial activation and systemic inflammation: I kappa B alpha degradation, induction of nitric oxide synthase, induction of proinflammatory mediators, and cardiovascular dysfunction. J. Immunol. 166:1248-1260.
21. Wyant T. L., M. K. Tanner, and M. B. Sztein. 1999. *Salmonella typhi* flagella are potent inducers of proinflammatory cytokine secretion by human monocytes. Infect. Immun. 67:3619-3624.
22. Cookson B. T., and M. J. Bevan. 1997. Identification of a natural T cell epitope presented by *Salmonella*-infected macrophages and recognized by T cells from orally immunized mice. J. Immunol. 158:4310-4319.
23. Gupta S, H. Vohra, B. Saha, C. K. Nain, and N. K. Ganguly. 1996. Macrophage-T cell interaction in murine salmonellosis: selective down-regulation of ICAN-1 and B7 molecules in infected macrophages and its probable role in cell-mediated immunity. Eur. J. Immunol. 26:563-570.
24. Komoriya K., N. Shibano, T. Higano, N. Azuma, S. Yamaguchi, and S. I. Aizawa. 1999. Flagella proteins and type III-exported virulence factors are the predominant proteins secreted into the culture media *Salmonella typhimurium*. Mol Microbiol. 34:767-779.
25. McSorley S. J., B. T. Cookson, and M. K. Jenkins. 2000. Characterization of CD4+ T cell responses during natural infection with *Salmonella typhimurium*. J. Immunol. 164:986-993.
26. Gewirtz A. T., P. O. Simon Jr, C. K. Schmitt, L. J. Taylor, C. H. Hagedom, A. D. O'Brien, A. S. Neish, and J. L. Madara. 2001. *Salmonella typhimurium* translocates flagellin across interstinal epithelia, inducing a proinflammatory response. J. Clin. Invest. 107:99-109.
27. Ciscci-Woolwine, F., P. F. McDermott, and S. B. Mizel. 1999. Induction of cytokine synthesis by flagella from Gram-negative bacteria may be dependent on the activation or differentiation state of human monocytes. Infect. Immun. 67:5176-5185.
28. McDermott, P. F., F. Ciscci-Woolwine, J. A. Snipes, and S. B. Mizel. 2000. High-affinity interaction between Gram-negative flagellin and a cell surface polypeptide results in human monocyte activation. Infect. Immun. 68:5525-5529.
29. Wyant, T. L., M. K. Tanner, and M. B. Sztein. 1999. Potent immunoregulatory effects of *Salmonella typhi* flagella on antigenic stimulation of human peripheral blood mononuclear cells. Infect. Immun. 67:1338-1346.
30. Ciacci-Woolwine, F., I. C. Blomfield, S. H. Richardson, and S. B. Mizel. 1998. *Salmonella* flagellin induces tumor necrosis factor alpha in a human promonocytic cell line. Infect. Immun. 66:1127-1134.

SUMMARY OF THE INVENTION

The inventors have discovered that by altering the expression of type 1 fimbriae in a bacterial strain, the immune response of a host organism to a foreign antigen expressed by such a strain can be modulated. Thus, the present invention is directed to a live attenuated bacterial strain that expresses a foreign antigen, and wherein the bacterial stain is characterized by decreased expression of Type 1 fimbriae. The inventors have shown that such a bacterial strain induces an enhanced Th2 type immune response in an individual to which the strain is administered.

The invention also is directed to a live attenuated bacterial strain that expresses a foreign antigen, and wherein the bacterial strain is characterized by increased expression of Type 1 fimbriae. The inventors have shown that such a bacterial strain also induces an enhanced Th2 type response in individuals to which the strain is administered.

The bacterial strains of the present invention comprise a polynucleotide that encodes an antigen. The antigen is derived from a pathogen that is not the same as the carrier bacteria. Pathogens from which the antigen may be derived include for example, worms and other helminths, fungi, viruses, protozoans, neoplastic cells and bacteria. Preferred pathogens from which the antigen may be derived include *Streptococcus pneumoniae, Streptococcus pyogenes, Streptococcus* group B, *Streptococcus mutans, Strptococcus sobrinus, Streptococcus equi, Erysipelothrix rhusiopathiae, Mycobacterium tuberculosis, Mycobacterium leprae, Listeria* spp., *Bacillus anthracis, Listeria monocytogenes, Clostridium* spp., *Corynebacterium diptheriae*, and *Mycoplasma* spp.

The bacterial strain may be any bacteria that can infect any of the mucosal membranes. The bacterial strain is preferably a gram negative bacteria and preferably is a member of the Enterobacteriaceae, Vibrionaceae, Francisellaceae, Legionalles, Pseudomonadaceae or Pasteurellaceae groups, including for example *Salmonella* spp., *Shigella* spp., *Escherichia* spp., *Yersinia* spp., and *Vibrio* spp. The bacterial strain preferably comprises a mutation that attenuates the virulence of the bacteria.

The invention is also directed to methods for modulating the immune response in an individual to an antigen. The method comprises administering to an animal a live attenuated bacterial strain that expresses a foreign antigen, wherein the strain is characterized by either decreased expression of Type 1 fimbriae or increased expression of Type 1 fimbriae. The immune response induced by such methods is characterized by increased production of IgG1 isotype antibodies to the heterologous antigen, thus indicating an enhanced Th2 type immune response. Preferably the individual is a human, livestock, poultry or pet.

BRIEF DESCRIPTION OF THE FIGURES

FIG. 7 shows the ΔfimA2119, ΔfimH1019 and ΔfimW113 chromosomal mutations.

FIG. 8 illustrates the construction of a suicide vector for introducing a defined deletion mutation, ΔfliC825, into the chromosome of *S. typhimurium* strains. The primers are shown in SEQ ID NOS 13-14, respectively, while the oligonucleotide is shown in SEQ ID NO: 22.

FIG. 9 illustrates the construction of a suicide vector for introducing a defined deletion mutation, ΔfljB217, into the chromosome of *S. typhimurium* strains. The primers are shown in SEQ ID NOS 15-18, respectively, in order of appearance.

FIG. 10 shows the ΔfliC825 and ΔfljB217 chromosomal mutations.

FIG. 11 is a graphic illustration of PspA specific IgG1 and IgG2a responses induced by live *S. typhimurium* vaccine strains.

DESCRIPTION OF THE INVENTION

Figure 1:
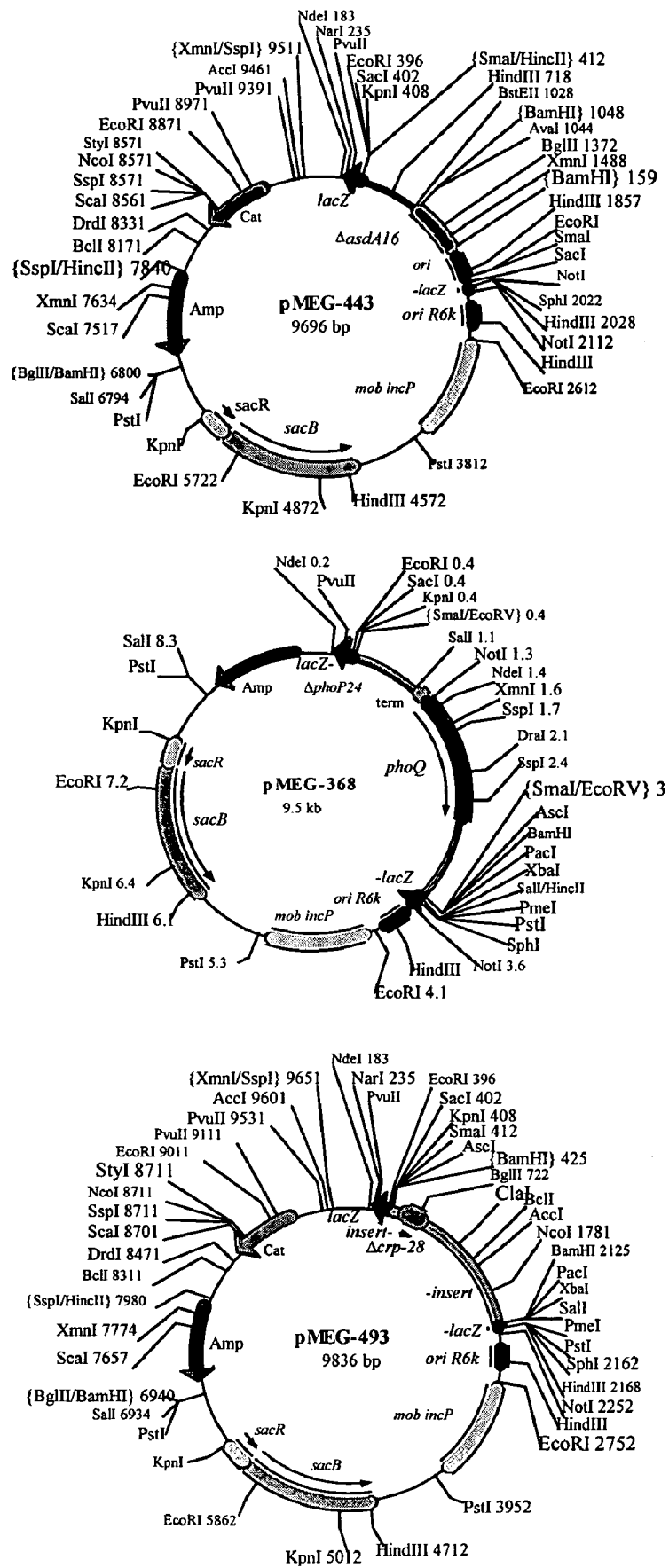
FIG. 1 shows diagrams of suicide vectors pMEG-368, pMEG-493 and pMEG-443. These vectors are used in the examples for transfer of the ΔphoP24 mutation, Δcrp-28 mutation and ΔasdA16 mutations, respectively.

Type 1 fimbriae are proteinaceous surface appendages that carry adhesions specific for mannosylated glycoproteins. These fimbriae are found on all members of the Enterobacteriaceae family. (Jones et al., 1995, *Proc. Nat. Acad. Sci.* USA 92:2081-2085) The bulk of the Type 1 fimbriae fiber is composed of FimA, and in the absence of the fimA gene that encodes that protein, Type 1 fimbriae are absent from the surface of the bacterial cell. Type 1 fimbriae also bear a mannose-binding FimH adhesion, encoded by the fimH gene. The fim complex also includes other genes that encode components that play roles in the biosynthesis of Type 1 fimbriae. Of particular significance is the fimW gene that encodes FimW. FimW is a negative regulator that effects Type 1 fimbriae expression. Bacterial strains harboring a mutation in the fimW gene exhibit a more strongly fimbriate phenotype than the wild-type parental strain. This increased fimbriae production is on the order of four- to eightfold over that of a wild-type strain. Tinker et al. (*J. Bacteriol.* 183: 435-442, 2001) describe the construction and characterization of a fimW mutant.

Other adhesins are expressed on the surface of bacterial cells, for example flagella. Flagella are important virulence factors and are also antigenic. Thus, alteration of expression of flagella in bacterial strains is expected to influence the immune response of an individual to a bacterial strain that expresses a foreign antigen. For example, genes involved in the synthesis of flagella, or encoding the structural components of flagella may be up or down regulated, or mutated such that they are inoperable. Bacterial strains harboring deletion mutations of the fliC and fljB genes exhibit a phenotype wherein flagella are substantially absent from the cell surface.

The invention is directed to live attenuated strains of bacteria that express a foreign antigen. The bacterial strains of the invention are modified such that the strains, in one embodiment, are characterized by decreased expression of Type 1 fimbriae, and in another embodiment, are characterized by increased expression of Type 1 fimbriae. The inventors have shown that by altering the expression of Type 1 fimbriae the immune response to the foreign antigen of an individual to which the strain is administered can be targeted to an enhanced Th2 type response. As used herein the term "individual" is intended to include all vertebrates, for example, mammals, including domestic animals and humans, various species of birds, including domestic birds, particularly those of agricultural importance.

In one embodiment of the invention, the bacterial strain comprises a mutation that renders the fimW gene inoperative. The bacterial strain comprising such a mutation is characterized by increased expression of Type 1 fimbriae. By "increased expression", it is meant that the bacterial strain has higher expression of Type 1 fimbriae than the wild-type parent strain from which it is derived. In preferred embodiments, the bacterial strain comprises a deletion mutation of the fimW gene. The inventors, as well as others, have determined that bacterial strains comprising such a deletion mutation express Type 1 fimbriae on the order of 4 to 8 fold higher than the wild-type parental strain. While mutations of the fimW gene are described in the Examples below, other means of decreasing the expression of the fimW gene are contemplated to be within the scope of the invention. For example, the promoter for the fimW gene could be mutated or deleted, or replaced with a regulatable promoter so as to down regulate the expression of the fimW gene.

As the Examples below illustrate, a live attenuated bacterial strain comprising a polynucleotide that expresses a foreign antigen and also comprising a deletion mutation of the fimW gene elicits an immune response that is characterized by an enhanced Th2 type response to the foreign antigen. An "enhanced Th2 type response" means that the immune response elicited by the live attenuated bacterial strain of the invention elicits an immune response in an individual to which the strain has been administered that is characterized by a greater IgG1 antibody response than is elicited in an individual to which a bacterial strain that is the same, but without the fimW deletion mutation has been administered. This increased IgG1 antibody titer is indicative of an enhanced Th2 type response.

Thus, one embodiment of the invention is directed to a live attenuated derivative of a bacterial strain wherein the bacterial strain comprises a polynucleotide that encodes a foreign antigen and further comprises a mutation that renders the fimW gene inoperative and is thus characterized by increased expression of Type 1 fimbriae, and the immune response to the foreign antigen is characterized by production of higher titers of IgG1 antibodies.

In another embodiment of the invention contemplated by the inventor, the bacterial strain comprises a mutation that renders the fimH gene inoperative. Such bacterial strains are characterized by decreased expression of the FimH adhesin of Type 1 fimbriae. By "decreased expression", it is meant that the bacterial strain has lower expression of the FimH adhesin of Type 1 fimbriae than the wild-type parent strain from which it is derived. In preferred embodiments the mutation is a deletion mutation. As the fimH gene encodes the FimH adhesin which binds to receptors on host cell surfaces, a bacterial strain comprising a fimH mutation would not have the ability to bind to host cells based on the complementarity between the FimH adhesin and its receptor. Thus, the inventor expects that the type of immune response that such a strain elicits to a foreign antigen expressed by the strain is altered, such that the response is characterized by increased IgG1 antibody titers.

In another embodiment of the invention, the bacterial strain comprises a mutation that renders the fimA gene inoperative. Such bacterial strains are characterized by decreased expression of FimA, the major structural component of Type 1 fimbriae. Bacterial cells harboring a fimA mutation lack Type 1 fimbriae on the surface of the cell. The Examples below illustrate that bacterial cells lacking Type 1 fimbriae elicit an immune response to a foreign antigen expressed by such a cell that is characterized by an enhanced Th2 type response.

The invention is also directed to a live attenuated derivative of a bacterial strain wherein the bacterial strain comprises a polynucleotide that encodes a foreign antigen, and further comprises mutations that render the fimH and the fimA genes inoperative. Such bacterial strains are characterized by decreased expression of Type 1 fimbriae. As the examples below illustrate, a live attenuated bacterial strain comprising a polynucleotide that encodes a foreign antigen and also comprises a deletion mutation of the fimH gene and a deletion mutation of the fimA gene elicits an immune response that is characterized by an enhanced Th2 type response to the foreign antigen. This enhanced Th2 type response is evidenced by increased IgG1 antibody titers.

Useful bacterial strains include any of the species of the Enterobacteriaceae family including *Alterococcus, Aquamonas, Aranicola, Arsenophonus, Brenneria, Bidvicia, Buttiauxella, Canditatus Phlomobacter, Cedeceae, Citrobacter, Edwardsiella, Enterobacter, Erwinia, Escherichia, Ewingella, Hafnia, Klebsiella, Kluyvera, Leclercia, Leminorella, Moellerella, Morganella, Obesumbacterium, Pantoea, Pectobacterium, Photorhabdus, Plesiomonas, Pragia, Proteus, Providencia, Rahnella, Raoultella, Salmonella, Samsonia, Serratia, Shigella, Sodalis, Tatumella, Trabulsiella, Wigglesworthia, Xenorhabdus, Yersinia* and *Yokenella*. Due to their clinical significance, *Escherichia, Shigella, Edwardsiella, Salmonella, Citrobacter, Klebsiella, Enterobacter, Serratia, Proteus, Morganella, Providencia* and *Yersinia* are considered to be particularly useful in the practice of the invention. Some embodiments of the instant invention comprise species of the *Salmonella* genera, as this genera has been widely and extensively studied and characterized.

The bacterial strains of the present invention comprise attenuating mutations. "Attenuated" refers to a reduced ability to elicit disease symptomology and disease in an individual, but which is still capable of attaching to, invading and persisting in appropriate lymphoid tissues within the individual. Attenuation thus enables the bacterial strains to expose the individual to the foreign antigen over an extended period of time. Attenuated strains are incapable of inducing a full suite of symptoms of the disease that is normally associated with its pathogenic counterpart.

The above described embodiments of the invention all comprise a polynucleotide that encodes a foreign antigen. Pathogens from which the foreign antigen may be derived include worms and other helminthes, fungi, viruses, protozoans, neoplastic cells, and bacteria. It is also contemplated that the bacterial strains of the present invention can be used to express antigens from non-pathogenic sources, for example gametes. Persons of skill in the art will recognize that antigens can be selected on the basis of various criteria. For example, for a highly specific or narrow spectrum immune response, the antigen preferably comprises an epitope that is found only in a particular pathogen or serotype. On the other hand, for a broad spectrum or general immune response the antigen preferably comprises an epitope or group of epitopes that is found in several pathogens or serotypes. Preferred pathogens include *Strptococcus pneumoniae, Erysipelothrix rhysiopathiae*, and *Mycobacterium tuberculosis*.

In preferred embodiments of the invention, the antigen comprises a polypeptide fragment of the pneumococcal surface protein A (PspA). The fragment of the PspA may comprise any antigenic fragment of any *Streptococcus pneumoniae* strain. Preferred fragments are the alpha helical domain of *Streptococcus pneumoniae* strain EF5688 (SEQ ID NO:19), the alpha helical domain of *Streptococcus pneumoniae* strain Rx1 (SEQ ID NO:20), or both (SEQ ID NO:21). Each of the afore-mentioned strains represents one of the two major families of *Streptococcus pneumoniae*. Therefore, the combination of PspA fragments from both strains is expected to provide an antigen that elicits an antibody immune response that would be protective against infection with a great diversity of *Streptococcus pneumoniae* capsular polysaccharide serotype strains.

The invention is also directed to methods for modulating the immune response to an antigen in an individual. The methods of the invention comprise administering to an individual any of the bacterial strains described above. Administration of the bacterial strains may be by any known technique including oral ingestion, gastric intubation, broncho-nasal-ocular spray or whole body spray. Any method whereby the live attenuated bacterial strain can reach the mucosal tissue and induce an immune response sufficient to confer protective immunity against the pathogen from which the foreign antigen is isolated is satisfactory. The dosages required will vary, and the skilled artisan will understand that routine experimentation will allow for such determination. It is also contemplated that more than one dose may be administered separated by a period of time, such that the desired level of immunity is induced.

EXAMPLES

Table 1 below describes the various bacterial strains referred to in the description and the Examples. Table 2 describes the various plasmids referred to in the description and the Examples. DNA manipulations were carried out as described in the procedures of Sambrook et al., 1989, Molecular Cloning, $2^{nd}$ ed. Cold Spring Harbor Laboratory Press, Cold Spring Harbor, N.Y. Bacteriophage P22HTint-mediated general transduction was performed by standard methods. Sternberg and Maurer, 1991, *Method. Enzymol.* 203:18-43; Schmieger and Backhaus, 1976, Mol. Gen. 143: 307-309. PCR amplification was employed to obtain DNA fragments for cloning and for verification of chromosomal deletion mutations. The PCR conditions were as follows: denaturation at 95 C for 20 sec.; primer annealing at 55 C for 20 sec.; polymerization at 72 C for 2 min.; and a final extension at 72 C for 10 min. Nucleotide sequencing reactions were performed using ABI prism fluorescent Big Dye Terminators® according to the manufacturer's instructions (PE Biosystems, Norwalk, Conn.).

TABLE 1

Bacterial strains

| Strain | Description | Genotype |
|---|---|---|
| χ3339 | *S. typhimurium* SL1344 wild-type, isolated from liver of moribund mouse after peroral inoculation. | Wild-type, hisG |
| χ4574 | *S. typhimurium* LT2 carrying atrB::MudJ insertion | atr B13::MudJ |
| χ8298 | Defined deletion derivative of *S. typhimurium* SL1344 containing Δpho24. Generated Δpho24 deletion by conjugating χ3339 with MGN-617 (pMEG-368). | hisG ΔphoP24 |
| χ8499 | Defined deletion derivative of *S. typhimurium* SL1344 containing Δcrp-28. Generated Δcrp-28 deletion by conjugating χ3339 with MGN-617 (pMEG-493). | hisG Δcrp-28 |
| χ8501 | Defined deletion derivative of *S. typhimurium* SL1344 containing Δcrp-28 ΔasdA16. Generated ΔasdA16 deletion by conjugating χ8499 with MGN-617 (pMEG-443). | hisG Δcrp-28 ΔasdA16 |
| χ8554 | Defined deletion derivative of *S. typhimurium* SL1344 containing ΔasdA16. Generated ΔasdA16 deletion by conjugating χ3339 with MGN-617 (pMEG-443). | hisG ΔasdA16 |
| χ8599 | Derivative of *S. typhimurium* SL1344 containing ΔasdA16 atrB13::MudJ. atrB13::MudJ allele from χ4574 was transduced into χ8554 by bacteriophage P22 HTint. | hisG ΔasdA16 atrB13::MudJ |
| χ8600 | Defined deletion derivative of *S. typhimurium* SL1344 containing ΔfliC825. Generated ΔfliC825 deletion by conjugating χ3339 with MGN-617 (pYA3547). | hisG ΔfliC825 |
| χ8601 | Defined deletion derivative of *S. typhimurium* SL1344 containing ΔfljB217. Generated ΔfljB217 deletion by conjugating χ3339 with MGN-617 (pYA3548). | hisG ΔfljB217 |
| χ8602 | Defined deletion derivative of *S. typhimurium* SL1344 containing ΔfliC825 ΔfljB217. Generated ΔfljB217 deletion by conjugating χ8600 with MGN-617 (pYA3548). | hisG ΔfliC825 ΔfljB217 |
| χ8610 | Defined deletion derivative of *S. typhimurium* SL1344 containing ΔfimW113. Generated ΔfimW113 deletion by conjugating χ3339 with MGN-617 (pYA3543). | hisG ΔfimW113 |

TABLE 1-continued

Bacterial strains

| Strain | Description | Genotype |
|---|---|---|
| χ8612 | Defined deletion derivative of *S. typhimurium* SL1344 containing ΔfliC825 ΔfljB217 Δpho24. Generated Δpho24 deletion by conjugating χ8602 with MGN-617 (pMEG-368). | hisG ΔfliC825 ΔfljB217 ΔphoP24 |
| χ8613 | Defined deletion derivative of *S. typhimurium* SL1344 containing ΔfliC825 ΔfljB217 ΔphoP24 ΔasdA16. Generated ΔasdA16 deletion by conjugating χ8612 with MGN-617 (pMEG-443). | hisG ΔfliC825 ΔfljB217 ΔphoP24 ΔasdA16 |
| χ8617 | Defined deletion derivative of *S. typhimurium* SL1344 containing ΔfimW113 Δpho24. Generated Δpho24 deletion by conjugating χ8610 with MGN-617 (pMEG-368). | hisG ΔfimW113 ΔphoP24 |
| χ8618 | Defined deletion derivative of *S. typhimurium* SL1344 containing ΔfimW113 Δpho24 ΔasdA16. Generated ΔasdA16 deletion by conjugating χ8617 with MGN-617 (pMEG-443). | hisG ΔfimW113 ΔphoP24 ΔasdA16 |
| χ8672 | Defined deletion derivative of *S. typhimurium* SL1344 containing ΔfimA2119. Generated ΔfimA2119 deletion by conjugating χ3339 with MGN-617 (pYA3544). | hisG ΔfimA2119 |
| χ8673 | Defined deletion derivative of *S. typhimurium* SL1344 containing ΔfimH1019. Generated ΔfimH1019 deletion by conjugating χ3339 with MGN-617 (pYA3545). | hisG ΔfimH1019 |
| χ8674 | Defined deletion derivative of *S. typhimurium* SL1344 containing ΔfimA2119 ΔfimH1019. Generated ΔfimH1019 deletion by conjugating χ8672 with MGN-617 (pYA3545). | hisG ΔfimA2119 ΔfimH1019 |
| χ8677 | Defined deletion derivative of *S. typhimurium* SL1344 containing ΔphoP24 ΔasdA16. Generated ΔasdA16 deletion by conjugating χ8298 with MGN-617 (pMEG-443). | hisG ΔphoP24 ΔasdA16 |
| χ8682 | Defined deletion derivative of *S. typhimurium* SL1344 containing ΔfimA2119 ΔfimH1019 ΔphoP24 ΔasdA16. Generated ΔasdA16 deletion by conjugating χ8683 with MGN-617 (pMEG-443). | hisG ΔfimA2119 ΔfimH1019 ΔphoP24 ΔasdA16 |
| χ8683 | Defined deletion derivative of *S. typhimurium* SL1344 containing ΔfimA2119 ΔfimH1019 ΔphoP24. Generated ΔphoP24 deletion by conjugating χ8674 with MGN-617 (pMEG-368). | hisG ΔfimA2119 ΔfimH1019 ΔphoP24 |
| χ6212 | *E. coli* K-12 ΔasdA4 strain derived from DH5α, following transduction with P1 from χ2981 to Tet resistance and Asd⁻. Fusaric acid resistant isolate was selected and confirmed to be Ap$^s$, Tet$^s$, and Asd⁻. | F⁻ λ⁻ φ80 Δ(lacZYA-argF) endA1 recA1 hsdR17 deoR thi-1 glnV44 gyrA96 relA1 ΔasdA4 |
| MGN-617 | *E. coli* K-12 ΔasdA4 strain derived from SM10λpir, following transduction with P1 from χ2981 to Tet resistance and Asd⁻. Fusaric acid resistant isolate was selected and confirmed to be Ap$^s$, Tet$^s$, and Asd⁻. | thi-1 thr-1 leub6 fhuA21 lavY1 glnV44 ΔasdA4 recA1 RP4 2-Tc::Mu [Δpir]; Km$^r$ |

*Streptococcus pneumoniae* WU2
Wild-type virulent, encapsulated type 3

TABLE 2

Plasmids

| Plasmids | Description |
|---|---|
| pDMS197 | A 5.6 kb suicide vector containing tetracycline-resistance and sacB. |
| pBlueScript SK⁺ | A 2.96 kb high copy number ColE1-based phagemid with ampicillin-resistance and blue/white color screening. |
| pGEM-3Z | A 2.7 kb ampicilin-resistance plasmid containing lacZ. |
| pMEG-149 | A pir dependent suicide vector which provides a light blue/white screen for inserts in MGN-026 and is mobilized by incP containing strains such as CC118 or SM10 lambda pir. |
| pMEG-359 | ΔphoP24 intermediate clone, obtained by digesting the inverse PCR clone pMEG-355, with Bg/II and EcoRI then ligating to the trpA terminator linkers. This clone no longer has a functional Pho⁺ phenotype on acid phosphatase soft agar overlay. |

TABLE 2-continued

Plasmids

| Plasmids | Description |
|---|---|
| pMEG-368 | A suicide vector for ΔphoP24 containing the 3.1 kb EcoRV fragment of pMEG-359 cloned into the SmaI site of pMEG149. This phoP24 deletion contains the trpA terminator with a new NotI site but does not modify the sequence of phoQ. |
| pMEG-375 | A chloramphenical and ampicillin resistant suicide vector derived from pMEG-149 by inserting the ~1.6 kb HincII-XmnI fragment of pYA800 containing the Cat gene of pACYC184 into the SspI site of pMEG-149. |
| pMEG-443 | A suicide vector for ΔasdA16 obtained by cloning ~1.5 kb HincII to SphI fragment of pMEG-006 containing ΔasdA16 and R6K ori into the SmaI-SphI site of suicide vector pMEG-375. |
| pMEG-493 | A suicide vector for Δcrp-28 containing the 1.8 kb SmaI-SphI fragment of pMEG-113 cloned into the SmaI-SphI site of pMEG-375. |
| pYA3543 | A suicide vector for ΔfimW113 obtained by cloning ~1.5 kb BamHI-HindIII fragment into BamHI-HindIII site of pBluescript SK$^+$ vector. Subsequently, the SacI-KpnI fragment was cloned into the suicide vector pDMS197. |
| pYA3545 | A suicide vector for ΔfimH1019 obtained by cloning ~1.1 kb KpnI-SacI PCR products into the KpnI-SacI site of suicide vector pDMS197. |
| pYA3547 | A suicide vector for ΔfliC825 obtained by cloning ~0.5 kb KpnI-SacI fragment from pYA3558 was cloned into the KpnI-SacI site of suicide vector pMEG-375 |
| pYA3548 | A suicide vector for ΔfljB217 obtained by cloning ~0.6 kb KpnI-SacI PCR product was cloned into the KpnI-SacI site of suicide vector pDMS197. |
| pYA3558 | A 1.4 kb HincII-PstI fragment containing fliC from pYA3557 was cloned into HincII-PstI pGEM-3Z. |

Example 1

Influence of Means of Attenuation on Type of Immune Response to an Expressed Recombinant Antigen Delivered by Attenuated *Salmonella* Vaccine Strains It has been demonstrated that the types of immunity induced by attenuated *Salmonella* vaccine strains expressing protective antigens encoded by genes from other pathogens can be influenced by the mode of attenuation. One frequently used means of attenuating bacterial pathogens is to introduce mutations for the cya and crp genes controlling catabolite repression (Curtiss and Kelly, 1987, *Infect. Immun.* 55:3035-3043). Strains with these mutations are defective in the uptake and metabolism of many carbon sources, peptides and other nutrients. The cya and crp genes also control other metabolic activities by the need for cAMP to complex with the Crp protein to cause transcription of genes governing nutrient uptake and catabolism as well as genes such as fur governing regulation of genes encoding proteins important for iron uptake as well as genes needed for the assembly and function of flagella and the synthesis and assembly of some fimbrial adhesins such as Type 1 fimbriae (Botsford and Harmon, 1992, *Microbial Rev.* 56:100-122). Attenuation due to a deletion of the phoP gene operates in a different manner by causing cells to be sensitized to killing within macrophages and in acidic environments (Miller et al., 1989, *Proc. Nat. Acad. Sci. USA.* 86:5054-5058; Groissman et al., 1989, *Proc. Nat. Acad. Sci. USA* 86:7077-7081). We had previously discovered that deletion mutations for the crp gene (Curtiss and Kelly, 1987, *Infect. Immun.* 55:3035-3043) or the phoP gene (Galan and Curtiss, 1989, Microbial Pathogen 6:433-443) rendered *Salmonella* avirulent for the mouse and highly immunogenic, in that animals immunized with high doses of a strain with either mutation suffered no ill effects but exhibited total immunity to subsequent challenge with 1000 times the lethal dose of the wild-type virulent *Salmonella* parent strain. Since *S. typhi* strains with the phoP mutation are more attenuated and immunogenic in human volunteers (Hohmann et al. 1999. *J. Inf. Dis.* 173:1408-1414) than *S. typhi* strains with the crp mutation, which can induce some disease symptomology in humans (Tacket et al. 1992. *Infect. Immun.* 60:536-541), we conducted comparative studies with *S. typhimurium* strains possessing defined deletion mutations in the crp gene and the phoP gene with regard to the type and magnitude of the immune response to the protective PspA antigen of *S. pneumoniae*.

Figure 2:
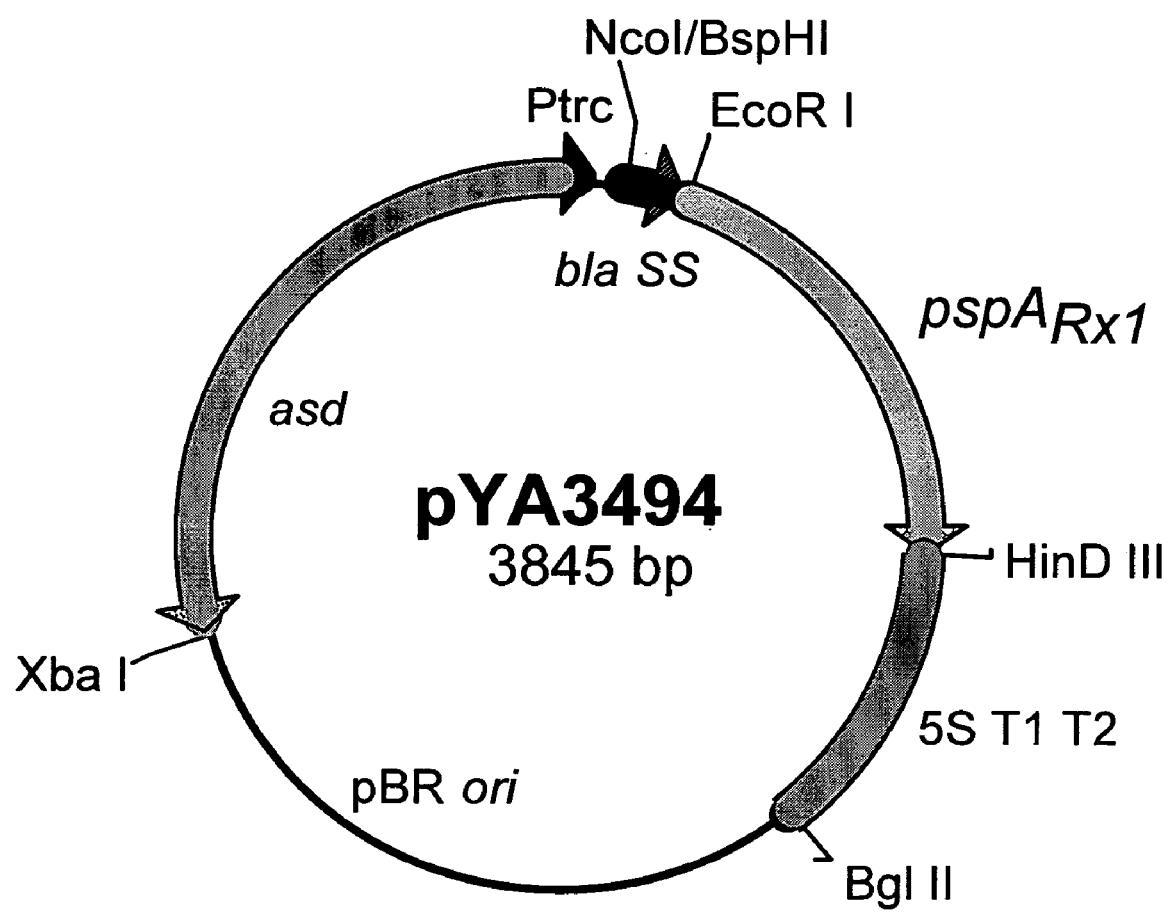
FIG. 2 shows a vector diagram of the Asd+ plasmid pYA3494 used in the examples.

All of the vaccine strains possessed the ΔasdA16 mutation which imposes an obligate requirement for diaminopimelic acid (DAP) to enable use of plasmid cloning vectors with the wild-type asd gene to result in a functional balanced-lethal host-vector system (Nakayama et al., 1988, Bio. Technol. 6:693-697; Galan et al., 1990, *Gene* 94:29-35) in the absence of expression of antibiotic resistance in the live vaccine, a condition not permissible by federal licensing agencies. Construction of χ8501 with the Δcrp-28 and the ΔasdA16 mutations has been described as has the construction of the ΔphoP24 mutation present in χ8677 along with the ΔasdA16 mutation. The suicide vectors pMEG-368 for transfer of the ΔphoP24 mutation, pMEG-493 for transfer of the Δ crp-28 mutation and pMEG-443 for transfer of the ΔasdA16 mutation are diagramed in FIG. 1. The recombinant Asd$^+$ plasmid pYA3494 (FIG. 2) was electroporated into χ8501 and χ8677. pYA3494 expresses the α-helical region of the PspA protein from *S. pneumoniae* strain Rx1 fused to the signal sequence and first 12 amino acids of β-lactamase. This construction causes approximately 50% of the PspA protein to be secreted across the cytoplasmic membrane of *S. typhimurium* with some 25% in the periplasmic space and the other 25% in the supernatant fluid in the absence of any cell lysis.

χ8677(pYA3494) and χ8501(pYA3494) were grown with gentle aeration in Luria broth at 37° C. until achieving an $OD_{600}$ of approximately 0.8. Bacterial cells were sedimented by centrifugation and suspended in BSG at a density such that a 20 µl inoculum would contain approximately $10^9$ CFU. Groups of five eight-week-old female BALB/c mice, that had been permitted to acclimate to our animal facility for one week, were deprived of food and water for 4 h and then orally immunized with 1×$10^9$ CFU of each vaccine strain. Food and water were returned 30 min after immunization. All the mice remained healthy and exhibited no disease symptomology throughout the period of experimental observation. Retro-orbital bleeding was used to collect serum samples to be analyzed by ELISA to quantitate antibody titers.

Figure 3:
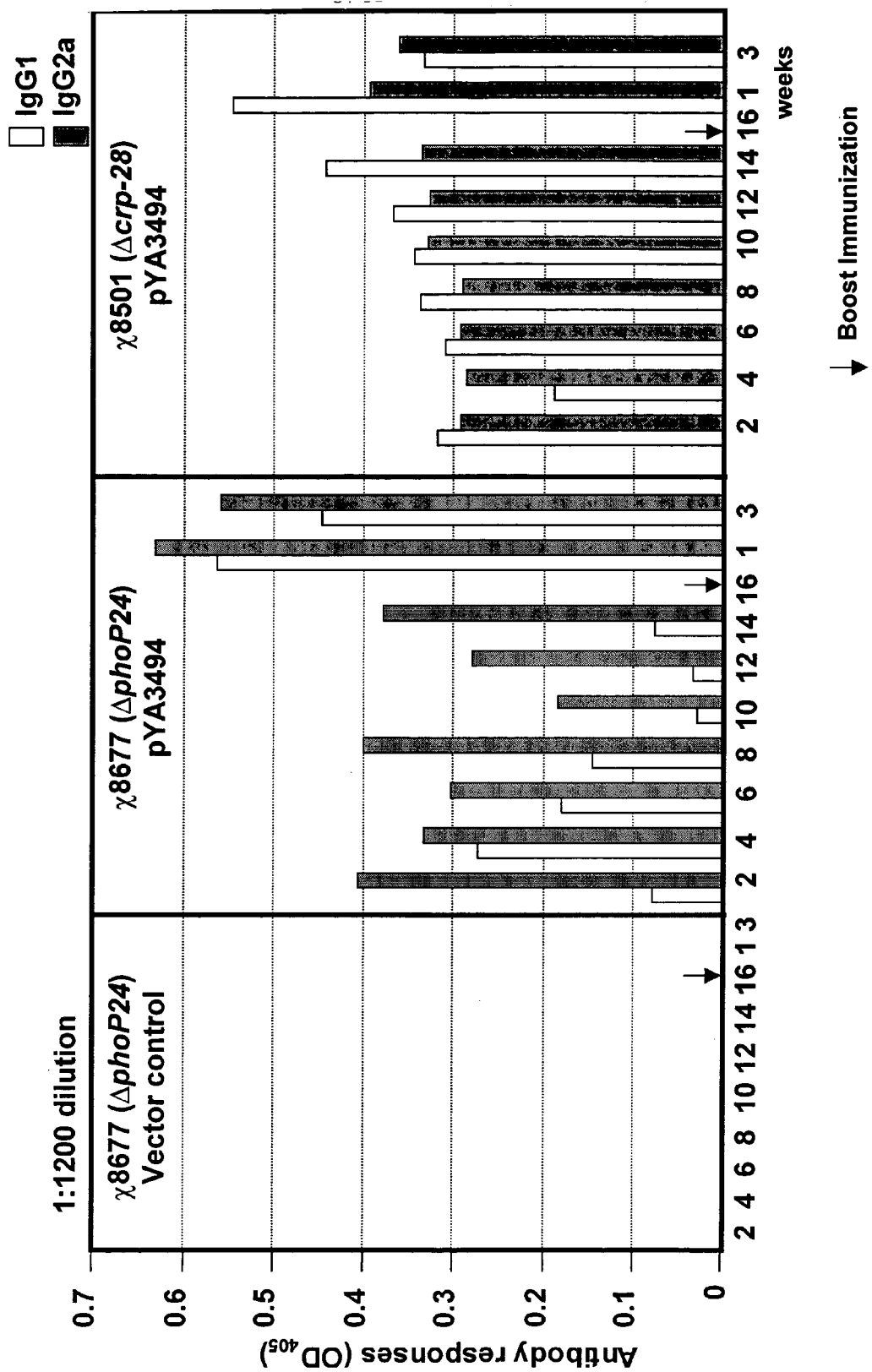
FIG. 3 is a graphic illustration of PspA specific IgG1 and IgG2a responses induced by live *S. typhimurium* vaccine strains.

For protective immunity against *S. pneumoniae* infection, it would be most desirable to elicit a Th2 type of immunity with induction of high titers of mucosal SIgA and serum IgG1 antibodies. Attenuated strains of *Salmonella* induce a predominant Th1 type of immunity and are thus excellent for delivery of protective antigens to induce a strong cellular immunity dependent upon either CD4$^+$ or CD8$^+$ T lymphocytes. The production of serum IgG1 antibody is characteristic of a Th2 mediated immunity whereas IgG2a is characteristic of a Th1 type of immunity. As revealed by the data in FIG. 3, the phoP24 strain χ8677 induced a predominant Th1 type of response to the pneumococcal PspA protein although following a booster immunization at 16 weeks, there was a significant increase in the titer of IgG1 antibodies against the PspA protein. In contrast, immunization with the Δcrp-28 strain χ8501 gave a mixed immune response but with at least 50% or more of the serum IgG1 class characteristic of the desired Th2 type of immunity. Since, as stated above, S. typhi strains with ΔphoP mutations are safer for immunization of humans then S. typhi strains with the Δcrp mutation, it was desirable to shift the predominant Th1 type response induced by χ8677 to a Th2 type of immunity. Since Δcrp strains do not synthesize flagellar proteins or exhibit motility and also are defective in synthesizing Type 1 fimbriae that permit bacterial cells to attach to mannosyl residues present on glycoproteins on the surface of many cell types including macrophages, we decided to determine whether deletion of genes for the synthesis of Type 1 fimbriae and/or flagella might shift the immune response induced by recombinant χ8677(pYA3494) to a more Th2 type of immune response.

Example 2

Figure 4:
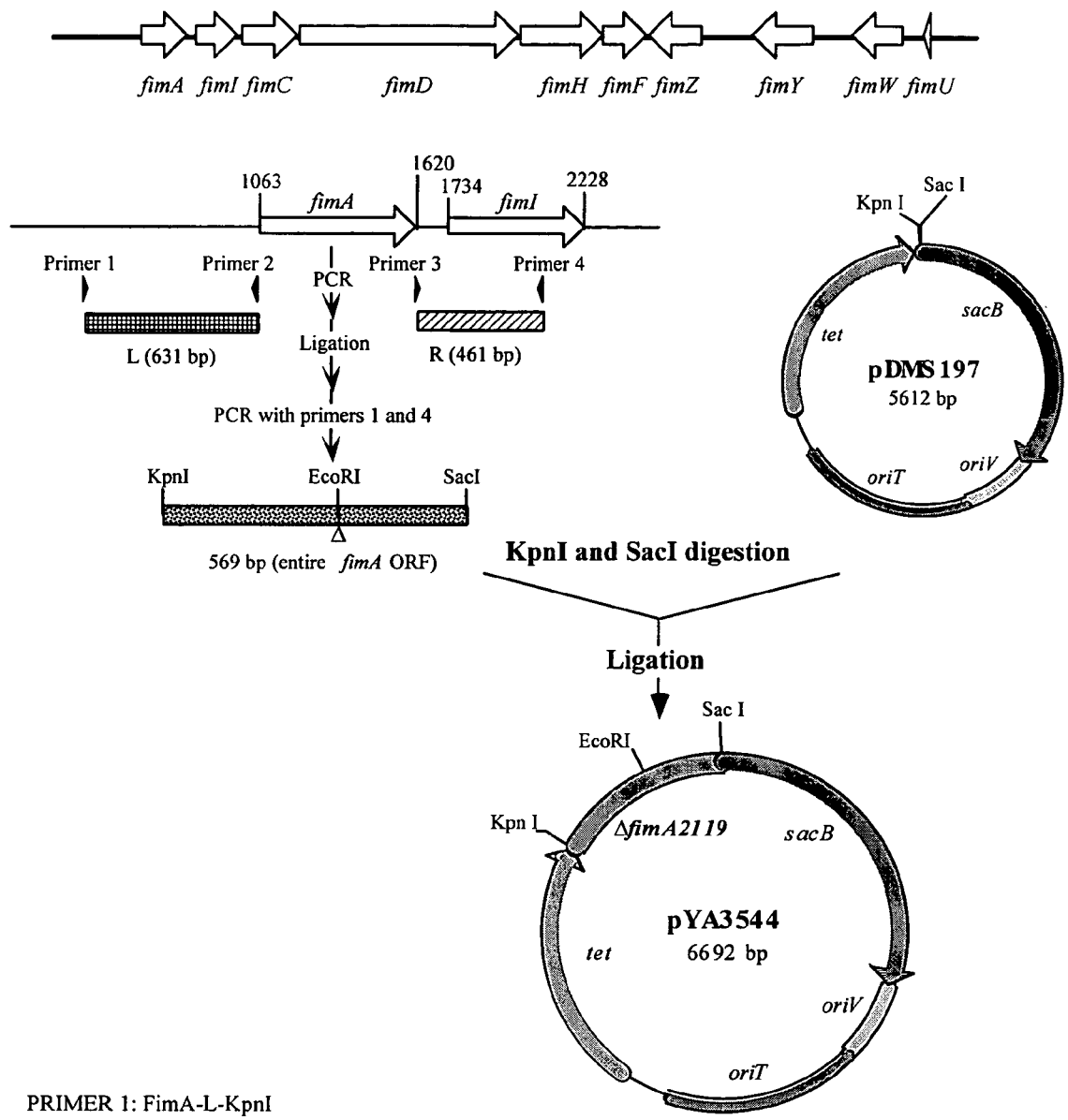
FIG. 4 illustrates the construction of a suicide vector for introducing a defined deletion mutation, ΔfimA2119, into the chromosome of *S. typhimurium* strains. The primers are shown in SEQ ID NOS 1-4, respectively, in order of appearance.

Generation of Suicide Vectors for Introducing Defined Deletion Mutations for fim Genes into the Bacterial Chromosome and Construction of Strains FIG. 4 diagrams the construction of a suicide vector to introduce a defined deletion mutation, ΔfimA2119, into the chromosome of S. typhimurium strains. The gene arrangement in the operon for Type 1 fimbriae is depicted at the top of FIG. 4. The fimA gene encodes the major component of Type 1 fimbriae and the absence of this gene results in the absence of Type 1 fimbriae from the surface of the bacterial cell. The strategy for constructing this deletion was to use primers 1 (SEQ ID NO:1) and 2 (SEQ ID NO:2) to PCR amplify a 631 bp fragment of DNA upstream to the fimA gene and which would possess KpnI and EcoRI restriction enzyme cleavage sites. Primers 3 (SEQ ID NO:3) and 4 (SEQ ID NO:4) (FIG. 4) were used to PCR amplify a 461 bp fragment of DNA downstream from the fimA gene that possessed EcoRI and SacI restriction enzyme cleavage sites. The two DNA fragments were digested with EcoRI and permitted to ligate. This product which contains a 569 bp deletion including the entire fimA ORF was PCR amplified using primers 1 and 4 and then cleaved with KpnI and SacI as was the suicide vector pDMS197 (FIG. 4). Products of these digestions were ligated to yield the suicide vector pYA3544 which was introduced into the suicide vector donor strain MGN-617 (Table 1). MGN-617 was then mated with χ3339 (Table 1) and recombinants inheriting the suicide vector by a single crossover event were selected by plating on L agar containing tetracycline. Ten tetracycline-resistant colonies were picked and purified. These isolates were grown to a density of about $10^8$ CFU as 1 ml cultures in L broth in the absence of tetracycline and then plated on L agar containing 5% sucrose to select for a second crossover event often to result in allele replacement with the ΔfimA2119 mutation replacing the wild-type fimA gene in the chromosome. Isolates were picked and characterized for defectiveness in exhibiting mannose-sensitive hemagglutination of yeast cells. Confirmation of the fimA deletion mutation was made by PCR analysis. χ8672 (Table 1) was saved for the next step in the construction.

Figure 5:
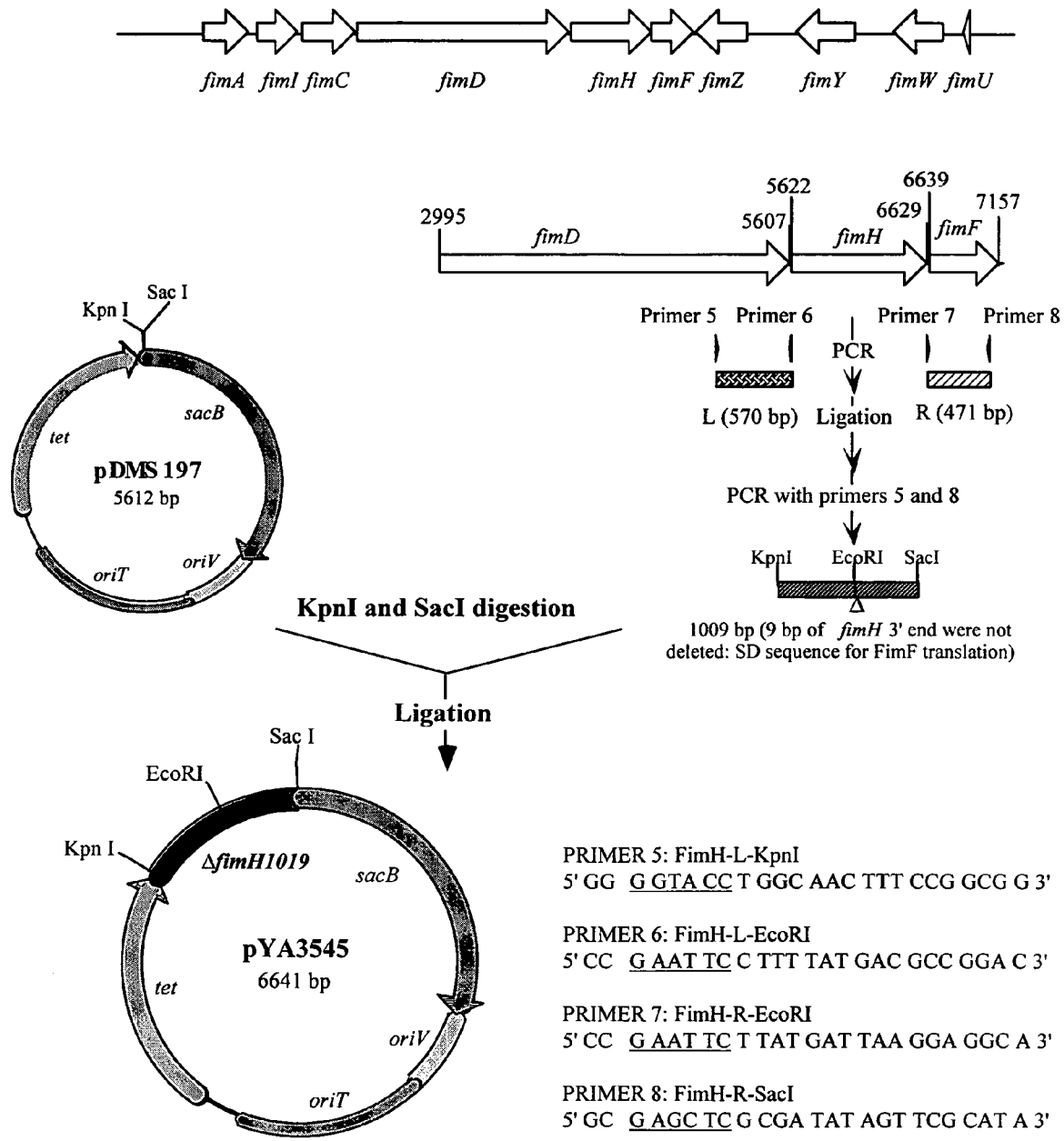
FIG. 5 illustrates the construction of a suicide vector for introducing a defined deletion mutation, ΔfimH1019, into the chromosome of *S. typhimurium* strains. The primers are shown in SEQ ID NOS 5-8, respectively, in order of appearance.

FIG. 5 diagrams the construction of the suicide vector to introduce a defined deletion mutation, ΔfimH1019 mutation, into the chromosome of S. typhimurium strains. The fimH gene encodes a minor protein that is responsible for the adhesiveness of bacteria expressing Type 1 fimbriae. It is the FimH protein that actually binds to the mannosyl residues on cell surface glycoproteins promoting the attachment of bacteria expressing and assembling Type 1 fimbriae. Primers 5 (SEQ ID NO:5) and 6 (SEQ ID NO:6) (FIG. 5) were used to PCR amplify a 570 bp fragment of DNA with terminal KpnI and EcoRI restriction enzyme recognition sequences. Primers 7 (SEQ ID NO:7) and 8 (SEQ ID NO:8) (FIG. 5) were used to PCR amplify a 471 bp fragment of DNA with terminal EcoRI and SacI restriction enzyme recognition sequences. The two DNA fragments were digested with EcoRI and the digestion products were ligated together after which the ligated DNA was PCR amplified using primers 5 and 8. This DNA fragment, which contains a 1009 bp deletion encompassing all of the fimH gene except for the C-terminal 9 bp that specifies part of the Shine-Dalgarno sequence to enable translation of the downstream fimF mRNA, was then digested with KpnI and SacI as was the suicide vector pDMS 197 (FIG. 5). The recombinant suicide vector pYA3545 resulting from ligation of these DNA molecules was introduced into the suicide vector donor strain MGN-617. MGN-617(pYA3545) was mated with χ8672 and tetracycline resistant transconjugants that had integrated pYA3545 into the chromosome by a single crossover event were selected on L agar plates containing tetracycline. Ten tetracycline-resistance colonies were picked and purified. Isolated colonies were inoculated into 1 ml of L broth and the cultures grown to a density of approximately $10^8$ CFU. These cultures were diluted and plated on L agar containing 5% sucrose to select for a second crossover event often accompanied by allele replacement to introduce the ΔfimH1019 mutation into the chromosome in place of the wild-type fimH gene. After testing for the correct phenotype and proof of the presence of the defined deletion by PCR analysis, χ8674 was stocked.

The ΔphoP24 mutation was introduced into χ8674 using the suicide vector pMEG-368 transferred by MGN-617 with the resulting strain designated as χ8683. The ΔasdA16 mutation was introduced into χ8683 using the suicide vector pMEG-443 transferred by MGN-617 with the resulting strain designated χ8682 (Table 1). Note that DAP must be present during the last step involving excision of pMEG-443 by selecting for sucrose resistance.

Figure 6:
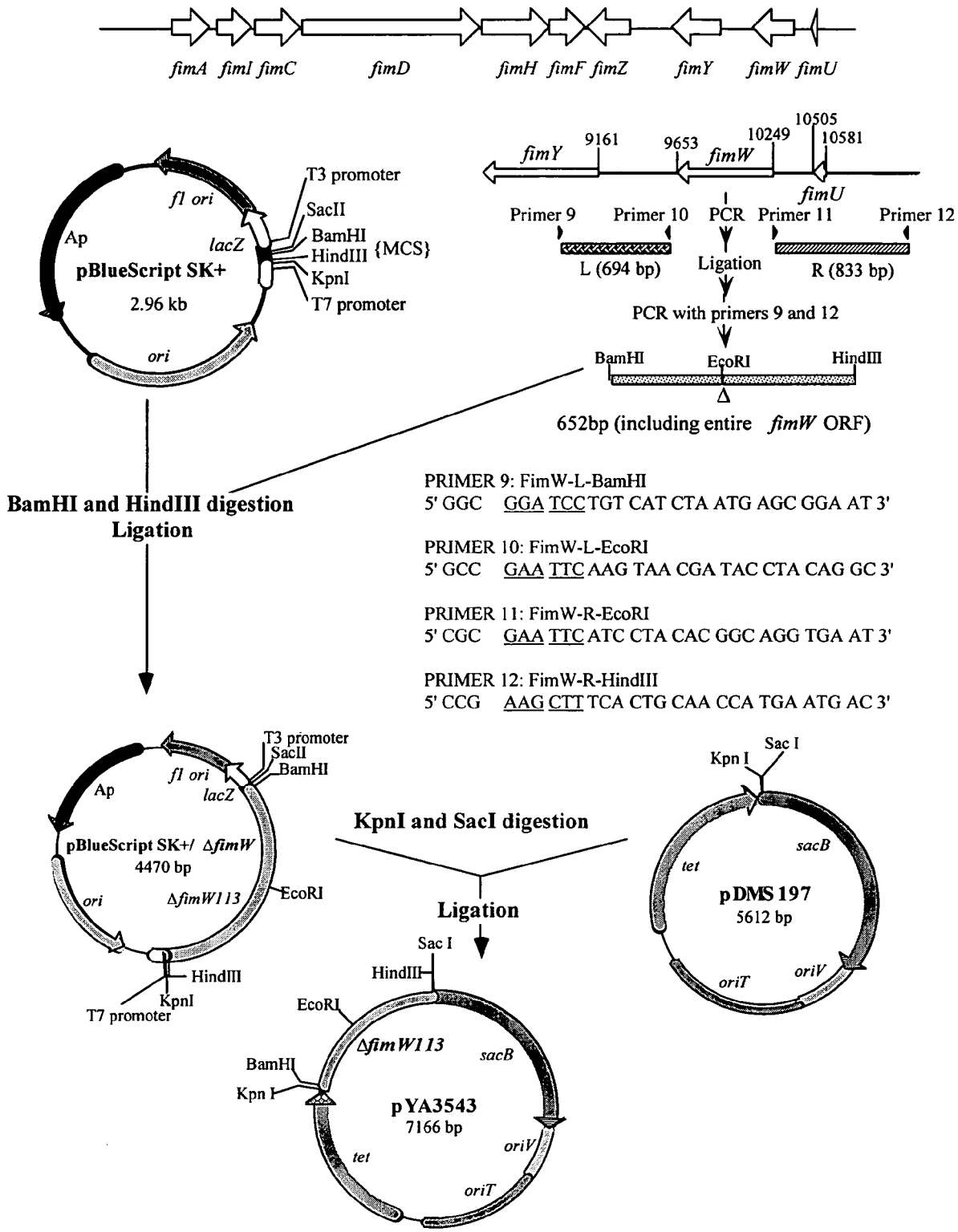
FIG. 6 illustrates the construction of a suicide vector for introducing a defined deletion mutation, ΔfimW113, into the chromosome of *S. typhimurium* strains. The primers are shown in SEQ ID NOS 9-12, respectively, in order of appearance.

As a further test of our hypothesis that the more Th2 type of immunity induced by strains possessing a Δcrp mutation would be due to the inability of such strains to synthesize Type 1 fimbriae, we decided to introduce a mutation that would cause hyper expression of Type 1 fimbriae with the expectation that that would cause a vaccine strain with the ΔphoP mutation to give a more enhanced Th1 type of immunity to the pneumococcal PspA protein. To test this hypothesis, we generated a defined deletion in the fimW gene, which encodes a repressor that down modulates expression of other genes in the fim operon. fimW mutants thus express three to eight times as many Type 1 fimbriae under a variety of conditions as do the wild-type strains. FIG. 6 diagrams the construction of the suicide vector to introduce a defined deletion mutation, ΔfimW113, into the chromosome of S. typhimurium strains. Primers 9 (SEQ ID NO:9) and 10 (SEQ ID NO:10) (FIG. 6) were used to amplify a 694 bp fragment of DNA downstream of the fimW gene with terminal BamHI and EcoRI restriction enzyme recognition sequences. Primers 11 (SEQ ID NO:11) and 12 (SEQ ID NO:12) (FIG. 6) were used to amplify an 833 bp fragment of DNA upstream to the fimW gene possessing terminal recognition sites for the EcoRI and HindIII restriction enzymes. These two DNA fragments were digested with EcoRI and ligated after which primers 9 and 12 (FIG. 6)

were used to PCR amplify this DNA fragment with terminal BamHI and HindIII restriction enzyme cleavage sites. This DNA fragment containing a 652 bp deletion including the entire fimW ORF was digested with BamHI and HindIII as was pBlueScript SK+ and the two DNA molecules ligated to yield pBlueScript SK+/ΔfimW (FIG. 6). pBlueScript SK+/ΔfimW was then digested with KpnI and SacI as was the suicide vector pDMS 197. These DNA fragments were ligated and the resulting plasmids were screened for the presence of tetracycline resistance and absence of ampicillin resistance. The plasmid pYA3543 was further evaluated by PCR for the presence of the DNA fragments flanking the fimW gene. pYA3543 was then introduced into the suicide vector donor strain MGN-617 (Table 1) which was mated with the S. typhimurium SL1344 strain χ3339 (Table 1). Ten tetracycline-resistant transconjugants that had integrated pYA3543 into the chromosome by a single crossover event were picked and purified on L agar containing tetracycline. Isolated colonies were picked into 1 ml of L broth and grown to a density of approximately $10^8$ CFU. These cultures were diluted and plated on L agar containing 5% sucrose to select isolates in which a second crossover had occurred to excise the suicide vector. In many cases, allele replacement would result in the inheritance of the ΔfimW113 allele in place of the wild-type fimW gene. Isolates were evaluated for hyper expression of Type 1 fimbriae as revealed by hyper hemagglutination of yeast cells and also for over expression of Type 1 fimbriae as observed by transmission electron microscopy using negative staining with phospho-tungstic acid. The selected strain was designated χ8610 (Table 1). χ8610 was further genetically manipulated for use in our studies first by introduction of the ΔphoP24 allele making use of transfer of the suicide vector pMEG-368 (FIG. 1) from MGN-617 (Table 1) with initial selection for ampicillin resistance of the single crossover event followed by selection for sucrose resistance for the second crossover to yield strain χ8617. The ΔasdA16 mutation was introduced into χ8617 using the suicide vector pMEG-443 (FIG. 1) transferred by MGN-617 with initial selection for chloramphenicol resistance and then sucrose resistance in the presence of DAP. The resulting strain with the ΔfimW113 ΔphoP24 and ΔasdA16 mutations was designated χ8618 (Table 1). FIG. 7 illustrates the chromosomal mutations ΔfimW2119, ΔfimH1019 and ΔfimW113 as used in constructions described herein.

Example 3

Generation of Suicide Vectors for Introducing Defined Deletion Mutations into the Bacterial Chromosome to Eliminate Synthesis of Flagella and Display of Motility and the Construction of Strains Since the crp mutation also causes non expression of synthesis and assembly of flagella, we investigated whether deletion of genes for flagellar synthesis might alter the immune response to the pneumococcal PspA protein delivered by a vaccine strain with the ΔphoP24 mutation. Since Salmonella exhibit phase variation with regard to expression of flagellar antigens, most serotypes of *Salmonella* possess two genes encoding different phase antigens with only one type produced by a given cell. A random switch enables cells expressing one phase antigen to express the other phase antigen. It is therefore necessary to design suicide vectors that would enable deletion of both genes encoding the two phase antigen types of *S. typhimurium.*

FIG. 8 diagrams the construction of the suicide vector pYA3547 for the introduction of the ΔfliC825 mutation. Primers 13 (SEQ ID NO:13) and 14 (SEQ ID NO:14) (FIG. 7) were used to PCR amplify a 1817 bp DNA fragment possessing terminal BamHI and SphI restriction enzyme cleavage sites. This DNA fragment contains the entire fliC coding sequence plus flanking sequences. This fragment was digested with BamHI and SphI as was the vector pGEM-3Z (FIG. 7). The two molecules were ligated to yield pYA3557. pYA3557 was digested with PstI, treated with T4 DNA polymerase to generate blunt ends and then digested with HincII. Blunt-end ligation yielded pYA3558 (FIG. 8) with a deletion of 1380 bp of the fliC gene (bp 39 through 1418). The fliC deletion was generated in such a way to be in frame so as not to interfere with expression of genes upstream and downstream from fliC gene that are in the same operon. pYA3558 and pMEG-375 were digested with BamHI and SphI and ligated to yield pYA3547 (FIG. 8). pYA3547 was confirmed by the presence of genes for chloramphenicol and ampicillin resistance, for sucrose resistance/sensitivity and the presence of the DNA fragment encompassing the ΔfliC825 mutation.

FIG. 9 diagrams the construction of the suicide vector pYA3548 for the introduction of the ΔfljB217 mutation. Primers 15 SEQ ID NO:15) and 16 (SEQ ID NO:16) (FIG. 9) were used to PCR amplify a 308 bp fragment of DNA encompassing the N-terminal region of the fljB gene and with terminal KpnI and EcoRI restriction enzyme recognition sequences. Primers 17 (SEQ ID NO:17) and 18 (SEQ ID NO:18) (FIG. 9) were used to generate a 312 bp fragment of DNA downstream from the fljB gene and having terminal EcoRI and SacI restriction enzyme recognition sequences. These two DNA fragments were digested with EcoRI and ligated. The ligation product was then PCR amplified with primers 15 and 18 (FIG. 9) to generate a 612 bp fragment of DNA possessing an internal deletion of 1247 bp within the fljB gene (bp 300 through bp 1546). This DNA fragment and the pDMS 197 vector DNA were digested with KpnI and SacI and ligated to each other to yield pYA3548 (FIG. 9) which is the suicide vector for delivery of the ΔfljB217 mutation. FIG. 10 illustrates the chromosomal mutations ΔfliC825 and ΔfljB217 as used in the constructions described herein.

To construct vaccine strains, the suicide vector pYA3547 (FIG. 8) was transferred to the suicide vector donor strain MGN-617 (Table 1) to transfer the suicide vector to the wild-type *S. typhimurium* SL1344 strain χ3339 (Table 1) which characteristically expresses the FliC flagellar phase antigen. Chloramphenicol-resistant colonies were selected by plating on L agar with chloramphenicol arising as a consequence of a single crossover integration of pYA3547 into the chromosome of χ3339. Ten colonies were picked and purified and isolated colonies picked into 1 ml L broth and grown to a density of approximately $10^8$ CFU. These cultures were diluted and plated on L agar containing 5% sucrose to recover isolates in which a second crossover event had occurred to eliminate the suicide vector from the chromosome. In many cases, this event is accompanied by allele replacement such that the ΔfliC825 allele replaces the wild-type fliC gene in the chromosome. Testing the sucrose-resistant isolates for inability to synthesize flagella or exhibit motility led to the stocking of χ8600 possessing the ΔfliC825 mutation. In order to introduce the fljB mutation it was first necessary to select a motile isolate of χ8600 that would express the FljB flagellar phase antigen. This was achieved by inoculating χ8600 onto the center of motility agar and isolating a motile swarm outgrowth after several days of incubation at 37° C. The suicide vector pYA3548 (FIG. 9) was transferred to the suicide vector donor strain MGN-617 to transfer the suicide vector to the motile derivative of χ8600 which was plated on L agar medium containing tetracycline. Ten tetracycline-resistant isolates were picked and purified and isolated colonies were used to inoculate 1 ml of L broth. Cultures were grown to a density of approximately $10^8$ CFU and were then diluted and plated on L agar containing 5% sucrose to result in a second crossover event excising the suicide vector from the chromosome. Many of these isolates would possess the ΔfljB217 allele in place of the wild-type fljB gene. Screening of these isolates for absence of flagella and display of motility identified the strain χ8602. The presence of the ΔfliC825 and fljB217 mutations in χ8602 was confirmed by PCR methodology. MGN-617(pMEG-368) described above was mated with χ8602 and ampicillin-resistant isolates were selected by plating on L agar with ampicillin. Ten ampicillin-resistant colonies were picked and purified and isolated colonies picked into 1 ml of L broth. Cultures were grown to an approximate density of $10^8$ CFU after which they were diluted and plated on L agar with 5% sucrose. Sucrose-resistant isolates in which a second crossover had occurred to excise the suicide vector from the chromosome were screened for the presence of the phoP mutation by an inability to synthesize acid phosphatase. χ8612 was stocked and the presence of the phoP24 mutation confirmed by PCR analysis. MGN-617(pMEG-443) described above was then mated with χ8612 with selection for chloramphenicol resistant isolates on L agar containing chloramphenicol. Ten chloramphenicol-resistant colonies were picked and purified. Isolated colonies were used to inoculate 1 ml L broth cultures that were grown to a density of approximately $10^8$ CFU. These cultures were diluted and plated on L agar containing DAP and 5% sucrose to select for a second crossover event arising due to excision of the suicide vector from the chromosome. Isolates were screened to identify those with an obligate requirement for DAP. One such isolate was stocked as χ8613. χ8613 was fully characterized for inability to synthesize flagella by western blot with flagella antiserum or exhibit motility, for the inability to synthesize acid phosphatase due to the phoP deletion and for an obligate requirement for DAP due to the asdA16 mutation. In addition, the presence all four mutations was confirmed by PCR analyses.

Example 4

Immunization of Mice and Quantitation of Immune Responses

Generally, inoculation of mice, bleeding of mice, and other experimental procedures such as growth of vaccine strains and ELISAs are according to standard methods as described herein or as generally known in the art.

The Asd+ plasmid pYA3494 (FIG. 2) was introduced into the S. typhimurium candidate vaccine strains χ8682, χ8618 and χ8613 whose constructions were described above in Examples 2 and 3. The vaccine strains χ8677(pYA3493) not expressing PspA and χ8677(pYA3494) expressing PspA were included as control strains attenuated by the ΔphoP24 mutation but having all the wild-type genes for Type 1 fimbriae, flagella and the display of motility.

Groups of five 8-week-old female BALB/c mice acclimated in our animal facility for one week prior to immunization were used for oral immunization with χ8677 (pYA3493), χ8677(pYA3494), χ8682(pYA3494), χ8618 (pYA3494), and χ8613(pYA3494). Each mouse received $1×10^9$ CFU suspended in 20 μl of BSG. A booster immunization at the same dose was administered 16 weeks after the primary immunization. All mice remained healthy and symptom free throughout the 19-week experiment. The titers of serum IgG1 indicative of a Th2 type response and serum IgG2a indicative of a Th1 type of response were determined from serum samples recovered from blood obtained by retro-orbital bleeding and diluted 1:1200. The data are presented in FIG. 11. In comparing the antibody titers from mice immunized with χ8682 to mice immunized with χ8677, it is clear that the absence of Type 1 fimbriae enhances a Th2 type of immunity that is significantly different with regard to the titers of IgG1 induced by χ8682 versus the χ8677 control strain. It therefore appears that the better Th2 type response induced by vaccine strains with the Δcrp-28 mutation (FIG. 3) is due in part to the inability to synthesize Type 1 fimbriae. A surprising discovery was made in evaluating the data for mice immunized with χ8618 that over expresses Type 1 fimbriae due to the presence of the ΔfimW113 mutation. We expected that over expression of Type 1 fimbriae would have engendered a stronger Th1 type immunity than observed for the vaccine strain χ8677. This predicted result was not realized (FIG. 11). On the contrary, it seems that over expression of Type 1 fimbriae, quite possibly in a constitutive manner in vivo, targets vaccine cells to antigen presenting cells that preferentially give a Th2 type of response as opposed to a Th1 type response.

The results with the vaccine strain χ8613 that is unable to express flagellar antigens is ambiguous since the results do not significantly differ from those obtained from mice immunized with χ8677(pYA3494) (FIG. 11). An additional means of evaluating the influence of presence or absence of flagella would be to introduce the ΔfliC825 and ΔfljB217 mutations into χ8682 and χ8618 to determine whether these mutations altered and especially might further enhance the Th2 type response to the PspA antigen. In any event, eliminating a very immunogenic Salmonella antigen should lessen the Salmonella antigens to which the immunized host responds and thus enhance the likelihood of a better immune response to the expressed PspA antigen.

Since genomic analyses of Salmonella serotypes whose genomes have been sequenced have revealed the presence of approximately 12 fimbrial operons in each serotype, some shared by all serotypes and some unique, it is possible that deletion of some of these other fimbrial operons or their constitutive over expression might be useful in further modulating the immune response by altering the types of antigen processing cells to which antigens are delivered. In some instances, this might further enhance a Th2 type response but in others could enhance a Th1 type of response to an expressed protective antigen encoded by genetic information from some other pathogen. In either case, this would significantly enhance the utility of recombinant attenuated Salmonella antigen delivery systems.

What is claimed is:

1. An immunogenic composition comprising a live attenuated derivative of a pathogenic Enterobacteriaceae bacteria, wherein (a) the attenuated derivative of a pathogenic Enterobacteriaceae bacteria comprises a polynucleotide that encodes an antigen of a pathogen that is different than the pathogenic Enterobacteriaceae bacteria, (b) the attenuated derivative of the pathogenic Enterobacteriaceae bacteria has increased expression of Type 1 fimbriae relative to the pathogenic Enterobacteriaceae bacteria from which the attenuated derivative was derived, and (c) the immunogenic composition elicits an enhanced Th2 immune response in an individual.

2. The immunogenic composition of claim 1 wherein the Enterobacteriaceae bacteria is selected from the group consisting of *Salmonella, Escherichia, Shigella* and *Yersinia*.

3. The immunogenic composition of claim 2 wherein the Enterobacteriaceae bacteria is *Salmonella enterica*.

4. The immunogenic composition of claim 3 wherein the attenuated derivative of a pathogenic Enterobacteriaceae bacteria comprises a mutation that causes increased expression of Type I fimbriae.

5. The immunogenic composition of claim 4 wherein the mutation is in a fimW gene wherein the mutation renders the fimW gene non-functional.

6. The immunogenic composition of claim 5 wherein the *Salmonella enterica* further comprises an attenuating mutation in a gene selected from the group consisting of crp, cya, asd, phoP, and dam.

7. The immunogenic composition of claim 6 wherein the gene is phoP.

8. The immunogenic composition of claim 1, further comprising a mutation in a fliC gene or a fljB gene, or both.

9. The immunogenic composition of claim 1, wherein the antigen is a polypeptide produced by a pathogen.

10. The immunogenic composition of claim 9, wherein the pathogen is selected from the group consisting of *Streptococcus pneumoniae, Streptococcus pyc genes, Streptococcus* group B, *Streptococcus mutans, Streptococcus sobrinus, Streptococcus equi, Erysipelothrix rhusiopathiae, Mycobacterium tuberculosis, Mycobacterium leprae, Listeria* spp., *Bacillus anthracis, Listeria monocytogenes, Clostridium* spp., *Corynebacterium diptheriae*, and *Mycoplasma* spp.

11. The immunogenic composition of claim 10, wherein the pathogen is *Streptococcus pneumoniae*.

12. The immunogenic composition of claim 11, wherein the antigen is pneumococcal surface protein A (PspA).

13. The immunogenic composition of claim 11, wherein the antigen is the alpha helical domain of *Streptococcus pneumoniae* strain EF5688 (SEQ ID NO:19), the alpha helical domain of *Streptococcus pneumoniae* strain Rx1 (SEQ ID NO:20), or both (SEQ ID NO:21).

14. The immunogenic composition of claim 11, wherein the antigen is SEQ ID NO:21.

15. A method of modulating the immune response of an individual comprising administering to said individual the immunogenic composition of claim 1.

16. A method of modulating the immune response of an individual comprising administering to said individual the immunogenic composition of claim 2.

* * * * *